(12) United States Patent
Mastrototaro et al.

(10) Patent No.: US 12,033,737 B2
(45) Date of Patent: Jul. 9, 2024

(54) STREAMED COMMUNICATION OF UPDATED CONTROL INFORMATION TO A MEDICAL DEVICE VIA AN INTERMEDIATE DEVICE

(71) Applicant: Medtronic MiniMed, Inc., Northridge, CA (US)

(72) Inventors: John J. Mastrototaro, Los Angeles, CA (US); Desmond Barry Keenan, Hollywood, CA (US); Benyamin Grosman, Winnetka, CA (US); Neha J. Parikh, West Hills, CA (US); Anirban Roy, Agoura Hills, CA (US); Do Kim, Sherman Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 52 days.

(21) Appl. No.: 17/313,849

(22) Filed: May 6, 2021

(65) Prior Publication Data
US 2021/0257076 A1   Aug. 19, 2021

Related U.S. Application Data

(63) Continuation of application No. 15/834,043, filed on Dec. 6, 2017, now Pat. No. 11,024,408, which is a
(Continued)

(51) Int. Cl.
*G16H 20/17* (2018.01)
*G05B 15/02* (2006.01)
(Continued)

(52) U.S. Cl.
CPC ............ *G16H 20/17* (2018.01); *G05B 15/02* (2013.01); *G16H 40/67* (2018.01); *G16Z 99/00* (2019.02)

(58) Field of Classification Search
None
See application file for complete search history.

(56) References Cited

U.S. PATENT DOCUMENTS

| 3,631,847 A | 1/1972 | Hobbs, II |
| 4,212,738 A | 7/1980 | Henne |
(Continued)

FOREIGN PATENT DOCUMENTS

| CN | 1713849 A | 12/2005 |
| CN | 101257450 A | 9/2008 |
(Continued)

OTHER PUBLICATIONS

Response to Examiner's Requisition dated Jan. 10, 2022, from counterpart Canadian Application No. 2921189, filed Apr. 12, 2022, 23 pp.

(Continued)

*Primary Examiner* — Nathan L Laughlin
(74) *Attorney, Agent, or Firm* — Weaver Austin Villeneuve & Sampson LLP

(57) ABSTRACT

A system includes one or more processors and one or more processor-readable storage media storing instructions which, when executed by the one or more processors, cause performance of: associating a medical device with an intermediate device, obtaining, from the medical device via the intermediate device, measurement data correlative to a condition of a user, determining updated control information for the medical device based at least in part on the measurement data, and streaming the updated control information to the medical device via the intermediate device.

20 Claims, 12 Drawing Sheets

Related U.S. Application Data continuation of application No. 13/972,803, filed on Aug. 21, 2013, now Pat. No. 9,880,528.

(51) Int. Cl.
*G16H 40/67* (2018.01)
*G16Z 99/00* (2019.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | Mcquilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Ill |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Ill et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Martiila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Van Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |

(56) References Cited

U.S. PATENT DOCUMENTS

| | | |
|---|---|---|
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | Delahuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,723,046 B2 | 4/2004 | Lichtenstein et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | Mcivor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV et al. |
| 8,603,026 B2 | 12/2013 | Favreau |
| 9,444,888 B2 | 9/2016 | Iyer |
| 9,880,528 B2 | 1/2018 | Mastrototaro et al. |
| 9,889,257 B2 | 2/2018 | Mastrototaro et al. |
| 11,024,408 B2 | 6/2021 | Mastrototaro et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1* | 6/2002 | Haller ............. A61N 1/37264 607/60 |
| 2002/0137997 A1 | 9/2002 | Mastrototaro et al. |
| 2002/0161288 A1 | 10/2002 | Shin et al. |
| 2003/0060753 A1 | 3/2003 | Starkweather et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0015132 A1 | 1/2004 | Brown |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |

(56) References Cited

U.S. PATENT DOCUMENTS

| | | |
|---|---|---|
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihal et al. |
| 2004/0263354 A1 | 12/2004 | Mann et al. |
| 2005/0038331 A1 | 2/2005 | Silaski et al. |
| 2005/0038680 A1 | 2/2005 | Mcmahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0078986 A1 | 4/2007 | Ethier et al. |
| 2007/0088521 A1 | 4/2007 | Shmuel et al. |
| 2007/0123819 A1 | 5/2007 | Mernoe et al. |
| 2007/0135866 A1 | 6/2007 | Baker et al. |
| 2007/0253021 A1 | 11/2007 | Mehta et al. |
| 2008/0071251 A1 | 3/2008 | Moubayed et al. |
| 2008/0154503 A1 | 6/2008 | Wittenber et al. |
| 2008/0249386 A1 | 10/2008 | Besterman et al. |
| 2008/0312512 A1 | 12/2008 | Brukalo et al. |
| 2009/0058635 A1 | 3/2009 | Lalonde et al. |
| 2009/0081951 A1 | 3/2009 | Erdmann et al. |
| 2009/0082635 A1 | 3/2009 | Baldus et al. |
| 2009/0153092 A1 | 6/2009 | Hosokawa et al. |
| 2009/0156991 A1 | 6/2009 | Roberts |
| 2010/0160861 A1 | 6/2010 | Causey, III et al. |
| 2010/0198842 A1 | 8/2010 | Giraudon et al. |
| 2010/0199162 A1* | 8/2010 | Boucard ............... H04L 9/3231 715/224 |
| 2011/0054391 A1 | 3/2011 | Ward et al. |
| 2011/0233393 A1 | 9/2011 | Hanson et al. |
| 2012/0016295 A1* | 1/2012 | Tsoukalis ............... G16H 20/17 604/66 |
| 2012/0271380 A1 | 10/2012 | Roberts et al. |
| 2012/0277667 A1 | 11/2012 | Yodat et al. |
| 2013/0046281 A1 | 2/2013 | Javitt |
| 2013/0142367 A1* | 6/2013 | Berry ..................... G16H 40/40 381/315 |
| 2013/0171938 A1* | 7/2013 | Mears ..................... H04B 7/26 455/41.2 |
| 2013/0188040 A1 | 7/2013 | Kamen et al. |
| 2013/0191513 A1* | 7/2013 | Kamen ................... H04L 67/02 709/219 |
| 2013/0203347 A1 | 8/2013 | Moosavi |
| 2013/0274705 A1 | 10/2013 | Burnes et al. |
| 2013/0294455 A1 | 11/2013 | Chen et al. |
| 2013/0317753 A1 | 11/2013 | Kamen et al. |
| 2014/0075015 A1* | 3/2014 | Chan ....................... H04L 41/22 709/224 |
| 2018/0101151 A1 | 4/2018 | Mastrototaro |

FOREIGN PATENT DOCUMENTS

| | | |
|---|---|---|
| CN | 101589393 A | 11/2009 |
| DE | 4329229 | 3/1995 |
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| EP | 2410448 A2 | 1/2012 |
| GB | 2218831 | 11/1989 |
| JP | 2010524050 A | 7/2010 |
| WO | WO 9620745 | 7/1996 |
| WO | WO 9636389 | 11/1996 |
| WO | WO 9637246 A1 | 11/1996 |
| WO | WO 9721456 | 6/1997 |
| WO | WO 9820439 | 5/1998 |
| WO | WO 9824358 | 6/1998 |
| WO | WO 9842407 | 10/1998 |
| WO | WO 9849659 | 11/1998 |
| WO | WO 9859487 | 12/1998 |
| WO | WO 9908183 | 2/1999 |
| WO | WO 9910801 | 3/1999 |
| WO | WO 9918532 | 4/1999 |
| WO | WO 9922236 | 5/1999 |
| WO | WO 0010628 | 3/2000 |
| WO | WO 0019887 | 4/2000 |
| WO | WO 0048112 | 8/2000 |
| WO | 02066101 A2 | 8/2002 |
| WO | WO 02058537 | 8/2002 |
| WO | WO 03001329 | 1/2003 |
| WO | 2003015838 A2 | 2/2003 |
| WO | WO 03094090 | 11/2003 |
| WO | WO 2005065538 | 7/2005 |
| WO | 2008097316 A1 | 8/2008 |

OTHER PUBLICATIONS

Office Action from counterpart Canadian Application No. 2,921,189 dated Jan. 10, 2022, 3 pp.

(Animas Corporation, 1999). Animas . . . bringing new life to insulin therapy. (Applicant points out, in accordance with MPEP 609.04(a), that the year of publication, 1999 is sufficiently earlier than the effective U.S. filing date, so that the particular month of publication is not in issue.).

(Intensive Diabetes Management, 1995). Insulin Infusion Pump Therapy. pp. 66-78. (Applicant points out, in accordance with MPEP 609.04(a), that the year of publication, 1995 is sufficiently earlier than the effective U.S. filing date, so that the particular month of publication is not in issue.).

(Medtronic MiniMed, 2002). Medtronic MiniMed Meal Bolus Calculator and Correction Bolus Calculator. International Version. (Applicant points out, in accordance with MPEP 609.04(a), that the year of publication, 2002 is sufficiently earlier than the effective U.S. filing date, so that the particular month of publication is not in issue.).

(Medtronic MiniMed, 2002). The 508 Insulin Pump a Tradition of Excellence. (Applicant points out, in accordance with MPEP 609.04(a), that the year of publication, 2002 is sufficiently earlier than the effective U.S. filing date, so that the particular month of publication is not in issue.).

(MiniMed Inc. 1999). MiniMed 508 Flipchart Guide to Insulin Pump Therapy. (Applicant points out, in accordance with MPEP 609.04(a), that the year of publication, 1999 is sufficiently earlier than The effective U.S. filing date, so that the particular month of publication is not in issue.).

(MiniMed Inc., 1999). Insulin Pump Comparison I Pump Therapy Will Change Your Life. (Applicant points out, in accordance with MPEP 609.04(a), that the year of publication, 1999 is sufficiently earlier than the effective U.S. filing date, so that the particular month of publication is not in issue.).

(MiniMed Inc., 2000). MiniMed® Now [I] Can Meal Bolus Calculator I MiniMed® Now [I] Can Correction Bolus Calculator. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Diabetes Management. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Pump Therapy. (Applicant points out, in accordance with MPEP 609.04(a), that the year of publication, 2000 is sufficiently earlier than the effective U.S. filing date, so that the particular month of publication is not in issue.).

(MiniMed International, 1998). MiniMed 507C Insulin Pump for those who appreciate the difference. (Applicant points out, in accordance with MPEP 609.04(a), that the year of publication, 1998 is sufficiently earlier than the effective U.S. filing date, so that the particular month of publication is not in issue.).

(MiniMed Technologies, 1994). MiniMed 506 Insulin Pump User's Guide. (Applicant points out, in accordance with MPEP 609.04(a),

(56) References Cited

OTHER PUBLICATIONS that the year of publication, 1994 is sufficiently earlier than the effective U.S. filing date, so that the particular month of publication is not in issue.).
(MiniMed Technologies, 1994). MiniMedrM Dosage Calculator Initial Meal Bolus Guidelines I MiniMed™ Dosage Calculator Initial Basal Rate Guidelines Percentage Method. 4 pages. (Applicant points out, in accordance with MPEP 609.04(a), that the year of publication, 1994 is sufficiently earlier than the effective U.S. filing date, so that the particular month of publication is not in issue.).
(MiniMed, 1996). FAQ: The Practical Things . . . . pp. 1-4. Retrieved on Sep. 16, 2003 from the WOrld Wide Web: http://web.archive.orglwebl19961111054546/www.minimed.com/fileslfag_pract.htm. (Applicant points out, in accordance with MPEP 609.04(a), that the year of publication, 1996 is sufficiently earlier than the effective U.S. filing date, so that the particular month of publication is not in issue.).
(MiniMed, 1996). MiniMedTM 507Insulin Pump User's Guide. (Applicant points out, in accordance with MPEP 609.04(a), that the year of publication, 1996 is sufficiently earlier than the effective U.S. filing date, so that the particular month of publication is not in issue.).
(MiniMed, 1996). The MiniMed 506. 7 pages. Retrieved on Sep. 16, 2003 from the World Wide Web: http:/lweb.archive.orglweb/19961111054527/www.minimed.comlfiles/506_pic.htm.
(Minimed, 1997). MiniMed 507 Specifications. 2 pages. Retrieved on Sep. 16, 2003 from the World Wide Web: http://web.archive.org/web/199701242348411www.minimed.comlfileslmmn075.htm.
(MiniMed, 1997). MiniMedrM 507 Insulin Pump User's Guide. (Applicant points out, in accordance with MPEP 609.04(a), that the year of publication, 1997 is sufficiently earlier than the effective U.S. filing date, so that the particular month of publication is not in issue.).
(MiniMed, 1997). Wanted: a Few Good Belt Clips! 1 page. Retrieved on Sep. 16, 2003 from the World Wide Web: http:l/web.archive.orglweb1199701242345591www.minimed.comlfileslmmn002.htm.
(MiniMed, 1998). MiniMed 507C Insulin Pump User's Guide. (Applicant points out, in accordance with MPEP 609.04(a), that the year of publication, 1998 is sufficiently earlier than the effective U.S. filing date, so that the particular month of publication is not in issue.).
(MiniMed, 2000). MiniMed® 508 User's Guide. Applicant points out, in accordance with MPEP 609.04(a), that the year of publication, 2000 is sufficiently earlier than the effective U.S. filing date, so that the particular month of publication is not in issue.).
Abel, P., et al., "Experience with an implantable glucose sensor as a prerequiste of an artificial beta cell," Biomed. Biochim. Acta 43 (1984) 5, pp. 577-584. (Applicant points out, in accordance with MPEP 609.04(a), that the year of publication, 1984 is sufficiently earlier than the effective U.S. filing date, so that the particular month of publication is not in issue.).
Bindra, Dilbir S., et al., "Design and in Vitro Studies of a Needle-Type Glucose Sensor for a Subcutaneous Monitoring," American Chemistry Society, 1991, 63, pp. 1692-1696. (Applicant points out, in accordance with MPEP 609.04(a), that the year of publication, 1991 is sufficiently earlier than the effective U.S. filing date, so that the particular month of publication is not in issue.).
Bode B W, et al. (1996). Reduction in Severe Hypoglycemia with Long-Term Continuous Subcutaneous Insulin Infusion in Type I Diabetes. Diabetes Care, vol. 19, No. 4, 324-327. (Applicant points out, in accordance with MPEP 609.04(a), that the year of publication, 1984 is sufficiently earlier than the effective U.S. filing date, so that the particular month of publication is not in issue.).
Boguslavsky, Leonid, et al., "Applications of redox polymers in biosensors," Sold State Ionics 60, 1993, pp. 189-197. (Applicant points out, in accordance with MPEP 609.04(a), that the year of publication, 1993 is sufficiently earlier than the effective U.S. filing date, so that the particular month ef publication is not in issue.).

Boland E (1998). Teens Pumping it Up! Insulin Pump Therapy Guide for Adolescents. 2nd Edition. (Applicant points out, in accordance with MPEP 609.04(a), that the year of publication, 1998 is sufficiently earlier than the effective U.S. filing date, so that the particular month of publication is not in issue.).
Brackenridge B P (1992). Carbohydrate Gram Counting a Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1992 is sufficiently earlier than the effective U.S. filing date, so that the particular month of publication is not in issue.).
Brackenridge, B P et al. (1995). Counting Carbohydrates How to Zero in on Good Control. MiniMed Technologies Inc. (Applicant points out, in accordance with MPEP 609.04(a), that the year publication, 1995 is earlier than the effective U.S. filing date, so that the particular month of publication is not in issue.).
Detlef Schoder et al. Core Concepts in Peer-to-Peer Networking. Peer to Peer Computing the Evolution of a Disruptive Technology. Rarnesh Subramanian and Brian D. Goodman. Editors. 2005, Chapter 1. pp. 1-27. Idea Group Inc .• Hershey. PA. ISBN 1-59140-429-0 (hard cover)—ISBN 1-59140-430-4 (soft cover)—ISBN 1-59140-431-2 (Ebook). (Applicant points out, in accordance with MPEP 609.04(a), that the year of publication, 2005 is sufficiently earlier than the effective U.S. filing date, so that the particular month of publication is not in issue.).
H-TRON® plus Quick Start Manual. (no date).
H-TRON®plus Reference Manual. (no date).
My Choice H-TRONplus Insulin Pump Reference Manual. (no date).
My Choice™ D-TRONTM Insulin Pump Reference Manual. (no date).
Farkas-Hirsch Ret al. (1994). Continuous Subcutaneous Insulin Infustion: a Review of the Past and Its Implementation for the Future. Diabetes Spectrum From Research to Practice, vol. 7, No.2, pp. 80-84, 136-138. (Applicant points out, in accordance with MPEP 609.04(a), that the year of publication, 1994 is sufficiently earlier than the effective U.S. filing date, so that the particular month of publication is not in issue.).
Geise, Robert J., et al., "Electropolymerized 1,3-diaminobenzene for the construction of a 1,1'-dimethylferrocene mediated glucose biosensor," Analytica Chimica Acta, 2B1, 1993, pp. 467-473. (Applicant points out, in accordance with MPEP 609.04(a), that the year of publication, 1993 is sufficiently earlier than the effective U.S. filing date, so that the particular month of publication is not in issue.).
Gernet, S., et al., "A Planar Glucose Enzyme Electrode," Sensors and Actuators, 17, 1989, pp. 537-540. (Applicant points out, in accordance with MPEP 609.04(a), that the year of publication, 1989 is sufficiently earlier than the effective U.S. filing date, so that the particular month of publication is not in issue.).
Gernet, S., et al., "Fabrication and Characterization of a Planar Electromechanical Cell and its Application as a Glucose Sensor," Sensors and Actuators, 18, 1989, pp. 59-70. (Applicant points out, in accordance with MPEP 609.04(a), that the year of publication, 1989 is sufficiently earlier than the effective U.S. filing date, so that the particular month of publication is not in issue.).
Gorton, L., et al., "Amperometric Biosensors Based on an Apparent Direct Electron Transfer Between Electrodes and Immobilized Peroxiases," Analyst, Aug. 1991, vol. 117, pp. 1235-1241. (Applicant points out, in accordance with MPEP 609.04(a), that the year of publication, 1991 is sufficiently earlier than the effective U.S. filing date, so that the particular month of publication is not in issue.).
Gorton, L., et al., "Amperometric Glucose Sensors Based on Immobilized Glucose—Oxidizing Enymes and Chemically Modified Electrodes," Analytica Chimica Acta, 249, 1991, pp. 43-54. (Applicant points out, in accordance with MPEP 609.04(a), that the year of publication, 1991 is sufficiently earlier than the effective U.S. filing date, so that the particular month of publication is not in issue.).
Gough, D. A., et al., "Two-Dimensional Enzyme Electrode Sensor for Glucose," Analytical Chemistry, vol. 57, No. 5, 1985, pp. 2351-2357. (Applicant points out; in accordance with MPEP 609.

(56) References Cited

OTHER PUBLICATIONS

04(a), that the year of publication, 1985 is sufficiently earlier than the effective U.S. filing date, so that the particular month of publication is not in issue.).
Gregg, Brian A., et al., "Cross-Linked Redox Gels Containing Glucose Oxidase for Amperometric Biosensor Applications," Analytical Chemistry, 62, Feb. 1990, pp. 258-263.
Gregg, Brian A., et al., "Redox Polymer Films Containing Enzymes. 1. a Redox- Conducting Epoxy Cement: Synthesis, Characterization, and Electrocatalytic Oxidation of Hydroquinone," The Journal of Physical Chemistry, vol. 95, No. 15, 1991, pp. 5970-5975. (Applicant points out, in accordance with MPEP 609.04(a), that the year of publication, 1991 is sufficiently earlier than the effective U.S. filing date, so that the particular month of publication is not in issue.).
HASHIGUCHI, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Hirsch I B et al. (1990). Intensive Insulin Therapy for Treatment of Type I Diabetes. Diabetes Care, vol. 13, No. 12, pp. 1265-1283. (Applicant points out, in accordance with MPEP 609.04(a), that the year of publication, 1990 is sufficiently earlier than the effective U.S. filing date, so that the particular month of publication is not in issue.).
Jacques L. Favreau, Dynamic Pulse-Width Modulation Motor Control and Medical Device Incorporating Same, U.S. Appl. No. 13/425,174, filed Mar. 20, 2012.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714. (Applicant points out, in accordance with MPEP 609.04(a), that the year of publication, 1992 is sufficiently earlier than the effective U.S. filing date, so that the particular month of publication is not in issue.).
Jonsson, G., et al., "An Electromechanical Sensor for Hydrogen Peroxide Based on Peroxidase Adsorbed on a Spectrographic Graphite Electrode," Electroanalysis, 1989, pp. 465-468. (Applicant points out, in accordance with MPEP 609.04(a), that the year of publication, 1989 is sufficiently earlier than the effective U.S. filing date, so that the particular month of publication is not in issue.).
Kanapieniene, J. J., et al., "Miniature Glucose Biosensor with Extended Linearity," Sensors and Actuators, B. 10, 1992, pp. 37-40. (Applicant points out, in accordance with MPEP 609.04(a), that the year of publication, 1992 is sufficiently earlier than the effective U.S. filing date, so that the particular month of publication is not in issue.).
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52. (Applicant points out, in accordance with MPEP 609.04(a), that the year of publication, 1988 is sufficiently earlier thar the effective U.S. filing date, so that the particular month of publication is not in issue.).
Koudelka, M., et al., "In-vivo Behaviour of Hypodermically Implanted Microfabricated Glucose Sensors," Biosensors & Bioelectronics 6, 1991, pp. 31-36. (Applicant points out, in accordance with MPEP 609.04(a), that the year of publication, 1991 is sufficiently earlier than the effective U.S. filing date, so that the particular month of publication is not in issue.).
Koudelka, M., et al., "Planar Amperometric Enzyme-Based Glucose Microelectrode," Sensors & Actuators, 18, 1989, pp. 157-165. (Applicant points out, in accordance with MPEP 609.04(a), that the year of publication, 1991 is sufficiently earlier than the effective U.S. filing date, so that the particular month of publication is not in issue.).
Kulkarni K et al. (1999). Carbohydrate Counting a Primer for Insulin Pump Users to Zero in on Good Control. MiniMed Inc. (Applicant points out, in accordance with MPEP 609.04(a), that the year of publication, 1999 is sufficiently earlier than the effective U.S. filing date, so that the particular month of publication is not in issue.).
Marcus A 0 et al. (1996). Insulin Pump Therapy Acceptable Alternative to Injection Therapy. Postgraduate Medicine, vol. 99, No. 3, pp. 125-142. (Applicant points out, in accordance with MPEP 609.04(a), that the year of publication, 1996 is sufficiently earlier than the effective U.S. filing date, so that the particular month of publication is not in issue.).
Mastrototaro, John J., et al. "An electroenzymatic glucose sensor fabricated on a flexible substrate," Sensors & Actuators, B. 5,1991, pp. 139-144. (Applicant points out, in accordance with MPEP 609.04(a), that the year of publication, 1991 is sufficiently earlier than the effective U.S. filing date, so that the particular month of publication is not in issue.).
Mastrototaro, John J., et al., "An Electroenzymatic Sensor Capable of 72 Hour Continuous Monitoring of Subcutaneous Glucose," 14th Annual International Diabetes Federation Congress, Washington D.C .. Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," AnnuaalInternational Conference ofteh IEEE Engineering in Medicine and Biology Society, Vo. 12, No. 2, 1990, pp. 483-484. (Applicant points out, in accordance with MPEP 609.04(a), that the year of publication, 1999 is sufficiently earlier than the effective U.S. filing date, so that the particular month of publication is not in issue.).
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-off Method for Patterning Enzyme-Immobilized Membranes in Multi-Biosensors," Sensors and Actuators 13, 1988, pp. 165-172. (Applicant points out, in accordance with MPEP 609.04(a), that the year of publication, 1988 is sufficiently earlier than the effective U.S. filing date, so that the particular month of publication is not in issue.).
Nishida, Kenro, et al., "Clinical applications often wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994 is sufficiently earlier than the effective U.S. filing date, so that the particular month of publication is not in issue.).
Nishida, Kenro, et al., "Development of a ferrocene-mediated needle-type glucose sensor covered with newly designed biocompatible membrane, 2-methacryloyloxyethylphosphorylcholine -co-n-butyl methacrylate," Medical Progress Through Technology, vol. 21, 1995, pp. 91-103. (Applicant points out, in accordance with MPEP 609.04(a), that the year of publication, 1995 is sufficiently earlier than the effective U.S. filing date, so that the particular month of publication is not in issue.).
Poitout, V., et al., "A glucose monitoring system for on line estimation on man of blood glucose concentration using a miniaturized glucose sensor implanted in the subcutaneous tissue and a wearable control unit," Diabetologia, vol. 36, published Jul. 1993, pp. 658-663.
Reach, G., "A Method for Evaluating in vivo the Functional Characteristics of Glucose Sensors," Biosensors 2, 1986, pp. 211-220. (Applicant points out, in accordance with MPEP 609.04(a), that the year of publication, 1986 is sufficiently earlier than the effective U.S. filing date, so that the particular month of publication is not in issue.).

(56) References Cited

OTHER PUBLICATIONS

Reed J et al. (1996). Voice of the Diabetic, vol. 11, No. 3, pp. 1-38. (Applicant points out, in accordance with MPEP 609.04(a), that the year of publication, 1986 is sufficiently earlier than the effective U.S. filing date, so that the particular month of publication is not in issue.).

Shaw, G. W., et al., "In vitro testing of a simply constructed, highly stable glucose sensor suitable for implantation in diabetic patients," Biosensors & Bioelectronics 6, 1991, pp. 401-406. (Applicant points out, in accordance with MPEP 609.04(a), that the year of publication, 1991 is sufficiently earlier than the effective U.S. filing date, so that the particular month of publication is not in issue.).

Shichiri, M., "A Needle-Type Glucose Sensor—a Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1998 is sufficiently earlier than the effective U.S. filing date, so that the particular month of publication is not in issue.).

Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1991 is sufficiently earlier than the effective U.S. filing date, so that the particular month of publication is not in issue.).

Shichiri, Motoaki, et al., "An artificial endocrine pancreas—problems awaiting solution for long-term clinical applications of a glucose sensor," Frontiers Med. Bioi. Engng., 1991, vol. 3, No. 4, pp. 283-292. (Applicant points out, in accordance with MPEP 609.04(a), that the year of publication, 1998 is sufficiently earlier than the effective U.S. filing date, so that the particular month of publication is not in issue.).

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Giycaemic Control in a Pacreatectomized Dogs with a Wearable Artificial Endocrine Pancreas," Diabetologia, vol. 24, 1983, pp. 179-184. (Applicant points out, in accordance with MPEP 609.04(a), that the year of publication, 1983 is sufficiently earlier than the effective U.S. filing date, so that the particular month of publication is not in issue.).

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: a useful Tool for Blood Glucose Monitoring in Diabetic Individuals," Diabetes Care, vol. 9, No. 3, May-Jun. 1986, pp. 298-301.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Dec. 1984, vol. 26, pp. 359-370.

Shichiri, Motoaki, et al., "Wearable Artificial Endocrine Pancreas with Needle-Type Glucose Sensor," The Lancet, Nov. 20, 1992, pp. 1129-1131.

Shinkai, Seiji, "Molecular Recognition of Mono- and Disaccharides by Phenylboronic Acids in Solvent Extraction and as a Monolayer," J. Chem. Soc., Chem. Commun., 1991, pp. 1039-1041. (Applicant points out, in accordance with MPEP 609.04(a), that the year of publication, 1991 is sufficiently earlier than the effective U.S. filing date, so that the particular month of publication is not in issue.).

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Skyler J S, "Continuous Subcutaneous Insulin Infusion [CSII] With External Devices: Current Status. Update in Drug Delivery Systems," Chapter 13, pp. 163-183, 1989, Futura Publishing Company. (Applicant points out, in accordance with MPEP 609.04(a), that the year of publication, 1989 is sufficiently earlier than the effective U.S. filing date, so that the particular month of publication is not in issue.).

Skyler J S et al. (1995). The Insulin Pump Therapy Book Insights from the Experts. MiniMed Technologies, (Applicant points out, in accordance with MPEP 609.04(a), that the year of publication, 1995 is sufficiently earlier than the effective U.S. filing date, so that the particular month of publication is not in issue.).

Sternberg, Robert, et al., "Study and Development of Multilayer Needle-type Enzyme—based Glucose Microsensors," Biosensors, vol. 4, 1988, pp. 27-40. (Applicant points out, in accordance with MPEP 609.04(a), that the year of publication, 1988 is sufficiently earlier than the effective U.S. filing date, so that the particular month of publication is not in issue.).

Strowig S M (1993). Initiation and Management of Insulin Pump Therapy. The Diabetes Educator, vol. 19, No. 1, pp. 50-60. (Applicant points out, in accordance with MPEP 609.04(a), that the year of publication, 1993 is sufficiently earlier than the effective U.S. filing date, so that the particular month of publication is not in issue.).

Tamiya, E., et al., "Micro Glucose Sensors using Electron Mediators Immobilized on a Polypyrrole-Moditied Electrode," Sensors and Actuators, vol. 18, 1989, pp. 297-307. (Applicant points out, in accordance with MPEP 609.04(a), that the year of publication, 1989 is sufficiently earlier than the effective U.S. filing date, so that the particular month of publication is not in issue.).

Tsukagoshi, Kazuhiko, et al., "Specific Complexation with Mono- and Disaccharides that can be Detected by Circular Dichroism," J. Org. Chem., vol. 56, 1991, pp. 4089-4091. (Applicant points out, in accordance with MPEP 609.04(a), that the year of publication, 1991 is sufficiently earlier than the effective U.S. filing date, so that the particular month of publication is not in issue.).

Ubran, G., et al., "Miniaturized thin-film biosensors using covalently immobilized glucose oxidase," Biosensors & Bioelectronics, vol. 6, 1991, pp. 555-562. (Applicant points out, in accordance with MPEP 609.04(a), that the year of publication, 1991 is sufficiently earlier than the effective U.S. filing date, so that the particular month of publication is not in issue.).

Urban, G., et al., "Miniaturized multi-enzyme biosensors integrated with pH sensors on flexible polymer carriers for in vivo applications," Biosensors & Bioelectronics, vol. 7, 1992, pp. 733-739. (Applicant points out, in accordance with MPEP 609.04(a), that the year of publication, 1992 is sufficiently earlier than the effective U.S. filing date, so that the particular month of publication is not in issue.).

Velho, G., et al., "In vivo calibration of a subcutaneous glucose sensor for determination of subcutaneous glucose kinetics," Diab. Nutr. Metab., vol. 3, 1988, pp. 227-233. (Applicant points out, in accordance with MPEP 609.04(a), that the year of publication, 1988 is sufficiently earlier than the effective U.S. filing date, so that the particular month of publication is not in issue.).

Walsh J, et al. (1989). Pumping Insulin: the Art of Using an Insulin Pump. Published by MiniMed Technologies. (Applicant points out, in accordance with MPEP 609.04(a), that the year of publication, 1989 is sufficiently earlier than the effective U.S. filing date, so that the particular month of publication is not in issue.).

Wang, Joseph, et al., "Needle-Type Dual Microsensor for the Simultaneous Monitoring of Glucose and Insulin," Analytical Chemistry, vol. 73, 2001, pp. 844-847. (Applicant points out, in accordance with MPEP 609.04(a), that the year of publication, 2001 is sufficiently earlier than the effective U.S. filing date, so that the particular month of publication is not in issue.).

Yamasaki, Yoshimitsu, et al., "Direct Measurement of Whole Blood Glucose by a Needle-Type Sensor," Clinics Chimica Acta, vol. 93, 1989, pp. 93-98. (Applicant points out, in accordance with MPEP

(56) References Cited

OTHER PUBLICATIONS 609.04(a), that the year of publication, 1989 is sufficiently earlier than the effective U.S. filing date, so that the particular month of publication is not in issue.).

Yokoyama, K., "Integrated Biosensor for Glucose and Galactose," Analytica Chimica Acta, vol. 218, 1989 pp. 137-142 (Applicant points out, in accordance with MPEP 609.04(a), that the year of publication, 1989 is sufficiently earlier than the effective U.S. filing date, so that the particular month of publication is not in issue.).

International Search Report from International Application No. PCT/US2002/03299, dated Dec. 31, 2002.

International Search Report from International Application No. PCT/US2014/050775, dated Jan. 19, 2015, 16 pp.

Prosecution History from European Patent Application No. 14755305.1, dated from Sep. 4, 2017 through Apr. 11, 2019, 190 pp.

Prosecution History from European Patent Application No. 19159057.9, dated from Jul. 29, 2019 through Jan. 20, 2020, 23 pp.

Prosecution History from U.S. Appl. No. 13/972,803, filed Mar. 24, 2016 through Dec. 18, 2017, 105 pp.

Prosecution History from U.S. Appl. No. 15/834,043, filed Apr. 1, 2020 through Oct. 1, 2020, 28 pp.

\* cited by examiner

STREAMED COMMUNICATION OF UPDATED CONTROL INFORMATION TO A MEDICAL DEVICE VIA AN INTERMEDIATE DEVICE

CROSS-REFERENCE TO RELATED APPLICATIONS

This application is a continuation of U.S. patent application Ser. No. 15/834,043, filed Dec. 6, 2017, which is a continuation of U.S. patent application Ser. No. 13/972,803, filed Aug. 21, 2013, the entire contents of each of which is incorporated by reference herein.

TECHNICAL FIELD

Embodiments of the subject matter described herein relate generally to medical devices, and more particularly, embodiments of the subject matter relate to dynamically updating the manner in which a medical device operates to regulate or otherwise influence a condition of an associated user based at least in part measurement data from that user.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user.

Over time, the needs of a particular user may change. For example, an individual's insulin sensitivity and/or insulin requirements may change as he or she ages or experiences lifestyle changes. Furthermore, each individual's needs may change in a manner that is unique relative to other users. While routine monitoring, doctor visits and manual adjustments to device settings may be performed to accommodate changes in an individual's needs, individuals often become discouraged from undertaking these activities on a frequent regular basis throughout their lifetime due to the amount of time and/or manual interaction involved. Accordingly, it is desirable to provide a fluid infusion device that is capable of adapting to suit the needs of its associated user with limited user impact.

BRIEF SUMMARY

In one example, a system includes one or more processors and one or more processor-readable storage media storing instructions which, when executed by the one or more processors, cause performance of: associating a medical device with an intermediate device, obtaining, from the medical device via the intermediate device, measurement data correlative to a condition of a user, determining updated control information for the medical device based at least in part on the measurement data, and streaming the updated control information to the medical device via the intermediate device.

In one example, a processor-implemented method includes associating a medical device with an intermediate device, obtaining, from the medical device via the intermediate device, measurement data correlative to a condition of a user, determining updated control information for the medical device based at least in part on the measurement data, and streaming the updated control information to the medical device via the intermediate device.

In one example, one or more non-transitory processor-readable storage media storing instructions which, when executed by one or more processors, cause performance of: associating a medical device with an intermediate device, obtaining, from the medical device via the intermediate device, measurement data correlative to a condition of a user, determining updated control information for the medical device based at least in part on the measurement data, and streaming the updated control information to the medical device via the intermediate device.

An embodiment of a medical device is provided. The medical device includes a motor, one or more data storage elements to maintain control information, and a control module coupled to the motor and the one or more data storage elements. The control module is configured to obtain updated control information via a peer-to-peer communication session over a network, store the updated control information in the one or more data storage elements, and thereafter operate the motor based at least in part on the updated control information.

In one embodiment, an apparatus for an infusion device is provided. The infusion device includes a motor operable to deliver fluid to a user, a sensing arrangement to obtain measurement data including one or more measured values indicative of a condition of the user, one or more data storage elements to maintain control information including a target value for the condition of the user and one or more control parameters. A control module is coupled to the motor, the sensing arrangement, and the one or more data storage elements, and the control module is configured to operate the motor to deliver the fluid to the user based at least in part on the one or more control parameters and a difference between the target value and a first value of the one or more measured values, wherein delivery of the fluid influences the condition of the user. The control module obtains updated control information including an updated target value for the condition of the user and one or more updated control parameters via a peer-to-peer communication session over a network, stores the updated control information in the one or more data storage elements, and thereafter operates the motor based at least in part on the one or more updated control parameters and a difference between the updated target value and a second value of the one or more measured values.

In another embodiment, a method of operating a medical device is provided. The method involves the medical device obtaining control information for regulating a condition of a user associated with the medical device via a peer-to-peer communication session over a network, obtaining a measured value for the condition of the user, and determining a command for operating the medical device based at least in part on the control information and the measured value.

In yet other embodiments, a system is provided that includes a medical device and a remote device. The medical device is operable to regulate a condition of a user. The remote device receives measurement data correlative to the condition of the user, determines control information for the medical device based at least in part on the measurement data, and transmits the control information via a first peer-to-peer communication session. The medical device receives the control information via a second peer-to-peer communication session and thereafter regulates the condition of the user based at least in part on the control information and subsequent measurement data.

In one embodiment, an infusion system is provided. The infusion system includes an infusion device, a remote device, and an intermediate device. The infusion device is operable to deliver fluid to a user, wherein the fluid influences a condition of the user. The remote device receives measurement data correlative to the condition of the user, determines control information for the infusion device based at least in part on the measurement data, and transmits the control information. The intermediate device receives the measurement data from the infusion device via a first peer-to-peer communication session over a first communications network, transmits the measurement data to the remote device via a second peer-to-peer communication session over a second communications network, receives the control information from the remote device via a third peer-to-peer communication session over the second communications network, and transmits the control information to the infusion device via a fourth peer-to-peer communication session over the first communications network. The infusion device receives the control information and thereafter delivers the fluid to the user to regulate the condition based at least in part on the control information and subsequent measurement data.

In yet another embodiment, a method of updating a medical device is provided. The method involves uploading measurement data from the medical device to a remote device, the measurement data comprising one or more measured values correlative to a condition of a user associated with the medical device, determining, by the remote device based at least in part on the measurement data, control information for regulating the condition of the user, initiating a peer-to-peer communication session with the medical device over a network, and providing the control information to the medical device via the peer-to-peer communication session.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and not necessarily drawn to scale.

DETAILED DESCRIPTION

Figure 1:
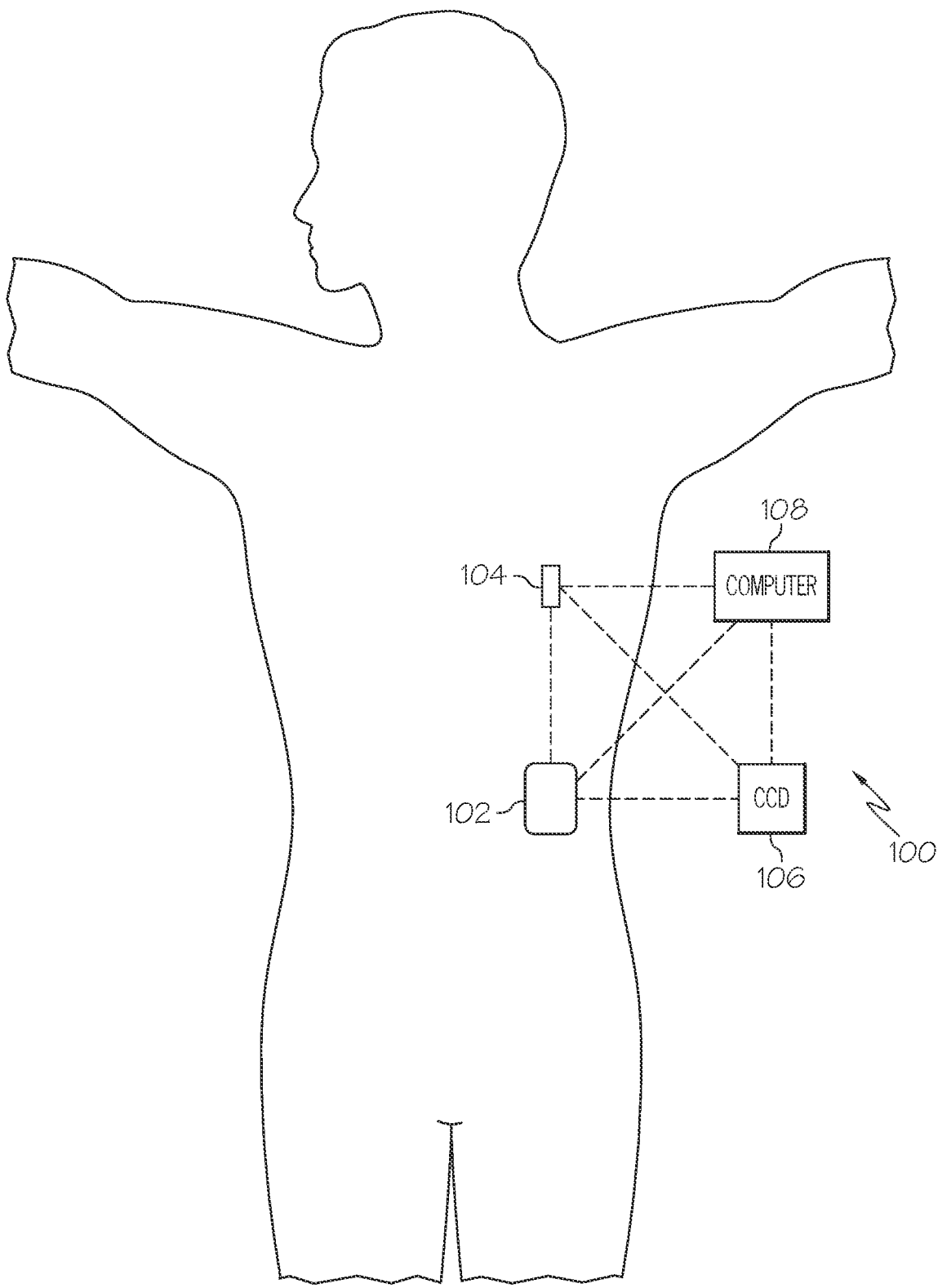
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented with any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097, 122; 6,485,465; 6,554,798; 6,558,320; 6,558,351; 6,641, 533; 6,659,980; 6,752,787; 6,817,990; 6,932,584; 7,402, 153; and 7,621,893, which are herein incorporated by reference. That said, the subject matter described herein is not limited to infusion devices and may be implemented in an equivalent manner for any medical device capable of regulating or otherwise influencing a condition of an associated user that wears or otherwise operates the medical device on his or her body.

Embodiments of the subject matter described herein generally relate to infusion devices that periodically and autonomously provide, to a remote device (alternatively referred to herein as a monitoring device), measurement data that quantifies, characterizes, or otherwise correlates to a condition of the user that is wearing or otherwise associated with the infusion device along with delivery data that quantifies or otherwise characterizes the delivery of fluid to the user by the infusion device. The monitoring device stores or otherwise maintains the measurement data and delivery data and analyzes the measurement data and delivery data to determine whether the manner in which the infusion device is operated to influence that condition should be modified or otherwise adjusted to improve regulation of that condition of the user. When the monitoring device determines the operation of the infusion device should be modified, the monitoring device determines updated control information for the infusion device and provides the updated control information to the infusion device. Thereafter, the infusion device executes or otherwise implements the updated control information, which, in turn, influences subsequent operation of the infusion device, and thereby influences regulation of the condition of the user in accordance with the updated control information. For example, the updated control information can include updated values for one or more parameters utilized by a control scheme or algorithm implemented by the infusion device to determine commands for operating the infusion device, an update to the control scheme or algorithm used by the infusion device to determine those operating commands, or a combination thereof.

As described in greater detail below, in exemplary embodiments, the infusion device utilizes closed-loop control to regulate the condition of the user by generating delivery commands for operating a motor to deliver a desired amount of fluid to the user based on a difference between a desired (or target) value for the condition and a measured value for the condition (or alternatively, a measured value that is correlative to the condition). In this regard, the infusion device periodically provides recently obtained measured values to the monitoring device along with recent delivery data, which, in turn, analyzes the recently obtained measured values and delivery data in conjunction with previously obtained measured values and delivery data to determine how values for gain coefficients, target values, or other parameters used by the closed-loop control should be adjusted to better regulate the condition of the user. The monitoring device determines and provides the updated parameter values to the infusion device, which, in turn, utilizes the updated parameter values in lieu of the previous parameter values when generating subsequent delivery commands, for example, by writing a new parameter value to a register associated with that parameter, thereby overwriting the previous parameter value.

As described in the context of FIGS. 8-13, in exemplary embodiments, temporary peer-to-peer communication sessions are utilized to upload recently obtained measurement data and delivery data from the infusion device to the monitoring device and to download updated control information to the infusion device from the monitoring device. In this regard, when the infusion device determines that recently obtained measurement data should be provided to the monitoring device, the infusion device autonomously initiates establishment of peer-to-peer communication sessions that are utilized to transmit the measurement data and delivery data to the monitoring device and terminated thereafter. Similarly, when the monitoring device determines that updated control information should be provided to the infusion device, the monitoring device autonomously initiates establishment of peer-to-peer communication sessions that are utilized to transmit the updated control information to the infusion device and terminated thereafter. The peer-to-peer communication sessions are established with an intermediate device that has been previously paired with the infusion device and provides an interface between a first communications network that the infusion device communicates on and another communications network on which the monitoring device communicates. For example, the infusion device may communicate on a personal area network (PAN) or another short range communications network while the monitoring device communicates on the Internet, a cellular network, or the like. In exemplary embodiments, the intermediate device automatically retransmits user-specific (or patient-specific) data and/or information received via the peer-to-peer communication sessions without permanently storing the data and/or information, such that the uploaded measurement data, the uploaded delivery data, and the downloaded control information are effectively streamed from/to the infusion device to/from the monitoring device via the intermediate device.

It should be noted that in practice, the closed-loop control schemes described herein may not be performed continuously by the infusion device. For example, a closed-loop control system may be disabled during intervals of time when the user is awake, alert, or otherwise able to manually operate the infusion device to control the condition of the user, with the closed-loop control being enabled to automatically regulate the condition of the user while the user is asleep or otherwise unable to manually operate the infusion device. In this regard, when the closed-loop control is disabled, the user may manually interact with the infusion device and operate the infusion device to deliver a bolus of fluid at the appropriate time of day or as needed. However, it should be appreciated that even when the closed-loop control is not enabled, the infusion device may continually obtain measurement data from its sensing arrangements and periodically upload the measurement data obtained while the closed-loop control is not enabled to the monitoring device along with delivery data and/or information indicative of the amount of fluid delivered by the infusion device and the timing of fluid delivery while the closed-loop control is not enabled. Accordingly, the monitoring device may utilize measurement data and delivery data that is obtained and uploaded by the infusion device while the closed-loop control is not enabled to determine updated values for control parameters, target values, and the like that will be downloaded to the infusion device and utilized by the infusion device to autonomously regulate the condition of the user when the closed-loop control is subsequently enabled.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108. For example, as described in greater detail below in the context of FIGS. 8-13, in some embodiments, the CCD 106 may function as an intermediate device that retransmits data and/or information between the infusion device 102 and the computer 108. For example, the infusion device 102 may transmit measurement data from the sensing arrangement 104 to the computer 108 via the CCD 106, and the computer 108 may transmit control information that influences or otherwise dictates operation of the infusion device 102 to the infusion device 102 via the CCD 106.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 may be configured to deliver fluid in response to the condition sensed by the sensing arrangement 104. In turn, the sensing arrangement 104 may continue to sense or otherwise quantify a current condition of the user, allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
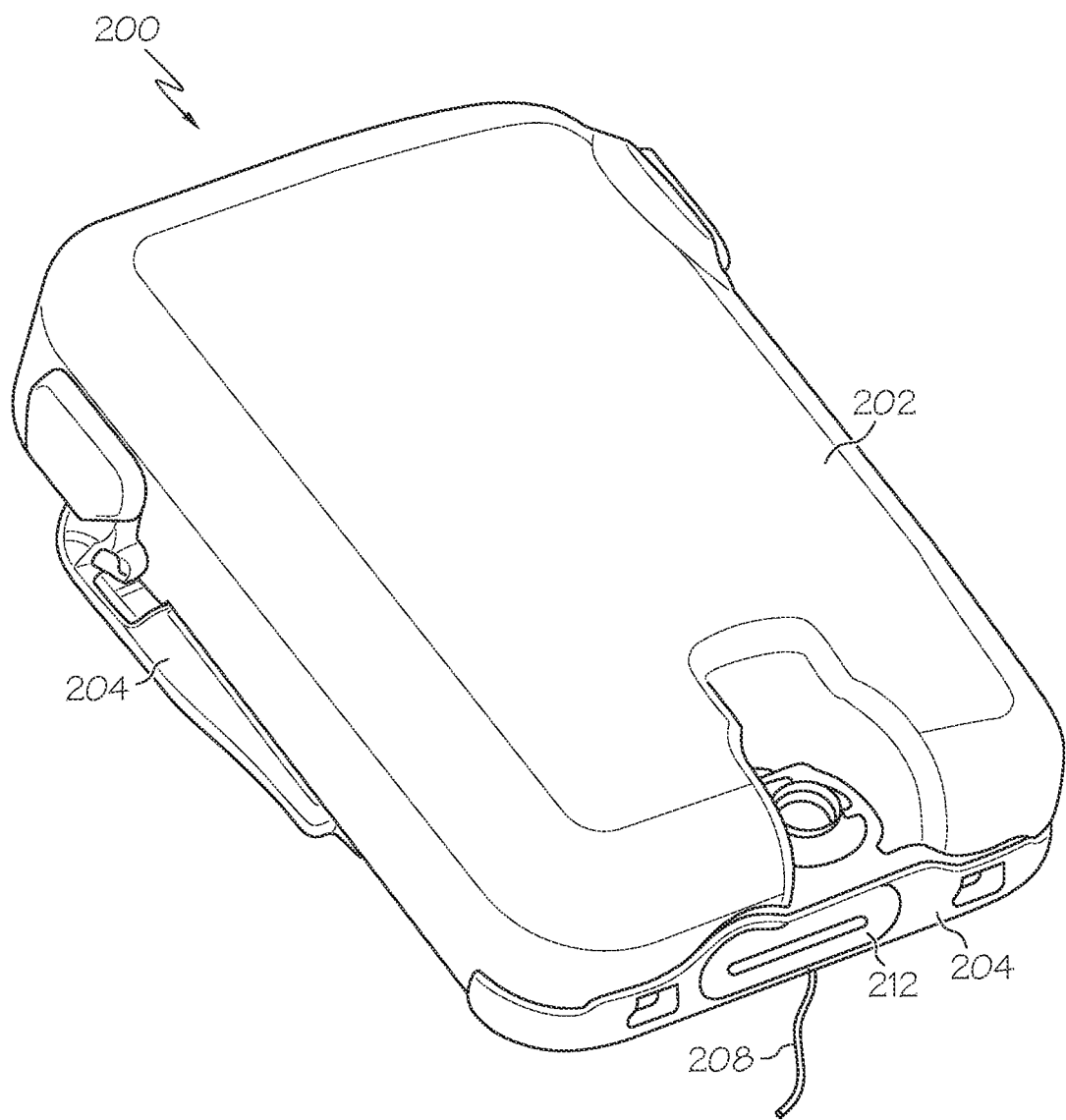
FIG. 2 is a perspective view of an exemplary embodiment of a fluid infusion device suitable for use in the infusion system of FIG. 1.
Figure 3:
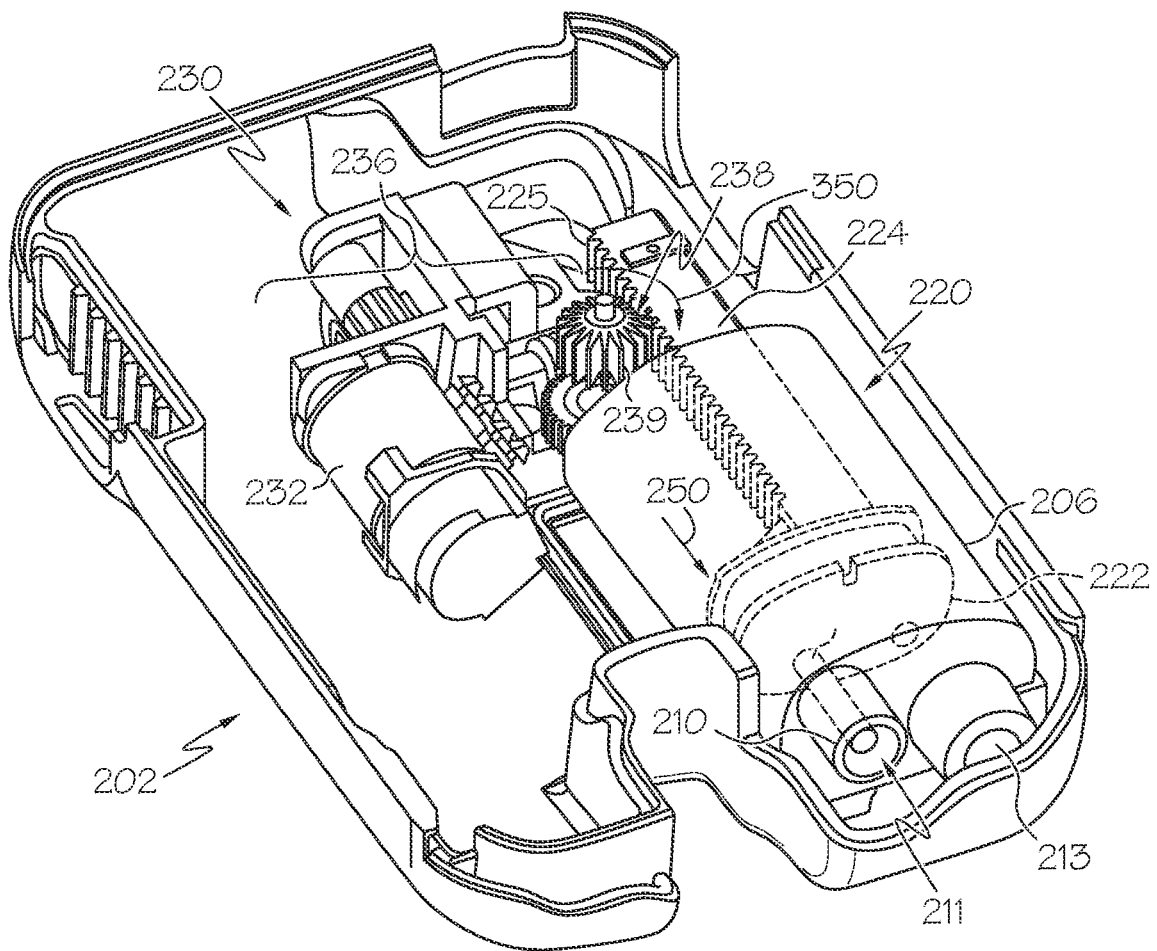
FIG. 3 is a perspective view that depicts the internal structure of the durable housing of the fluid infusion device shown in FIG. 2.

FIGS. 2-6 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a gear 238 of a drive system 230 contained in the durable housing 202. In this regard, the shaft 224 functions as a rack gear as part of a rack and pinion gear configuration. Although the subject matter may be described herein in the context of the shaft 224 being integral with or otherwise part of the plunger 222, in practice, the shaft 224 and the plunger 222 may be provided separately.

Figure 4:
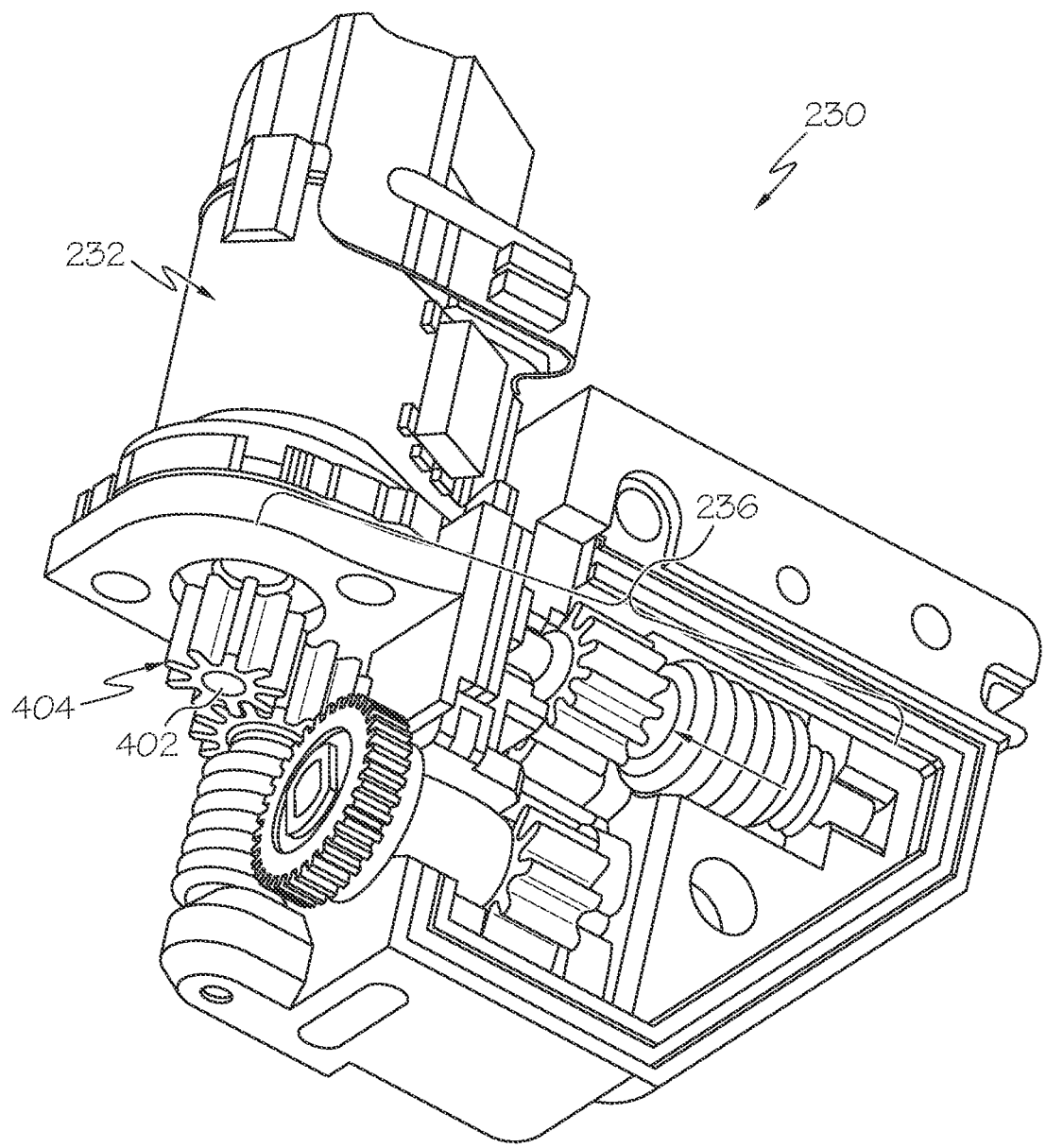
FIG. 4 is a perspective view of the drive system in the durable housing of the fluid infusion device of FIGS. 2-3.
Figure 5:
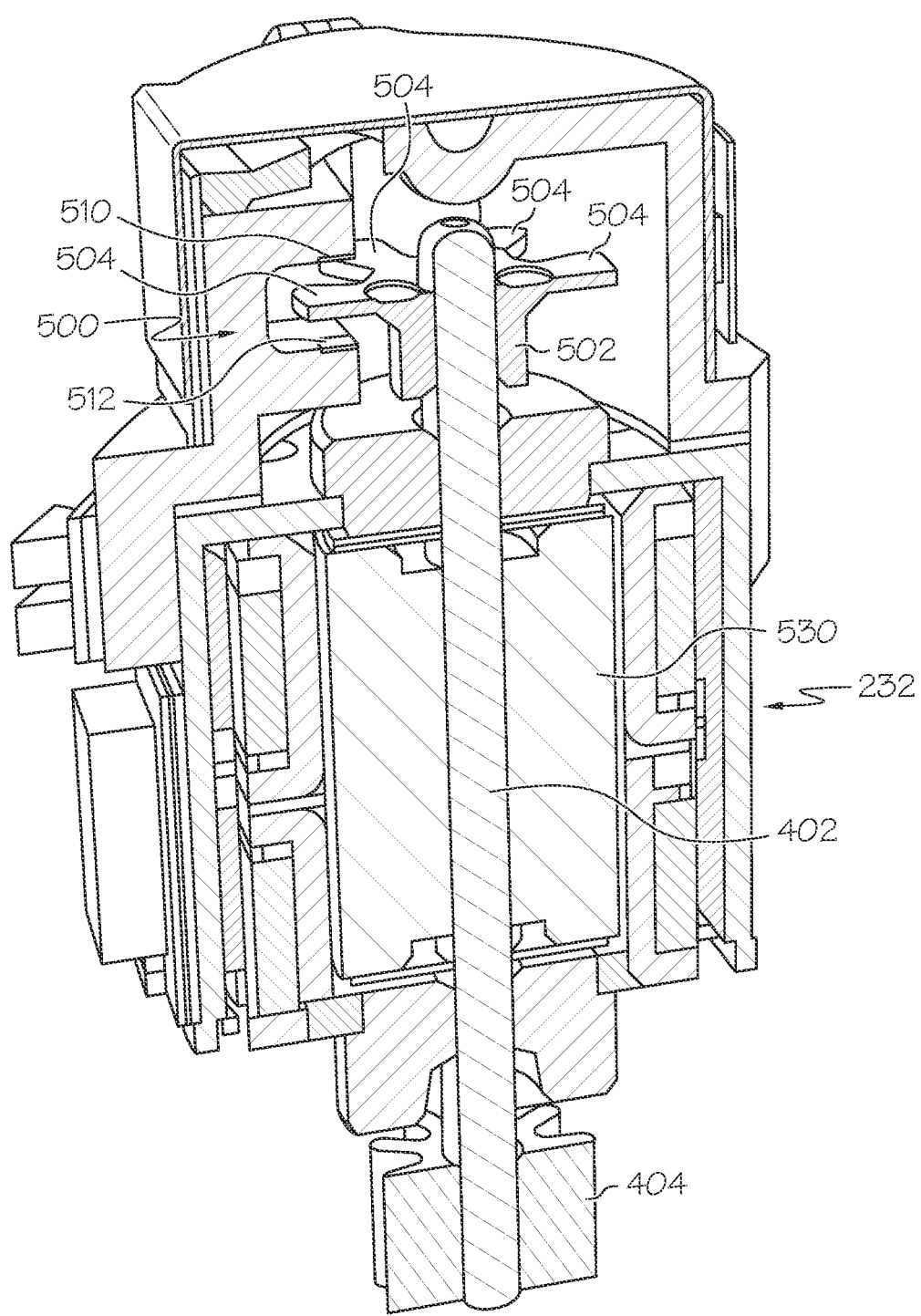
FIG. 5 is cross-sectional perspective view of the motor of drive system of FIG. 4 illustrating a sensor integrated therein.
Figure 6:
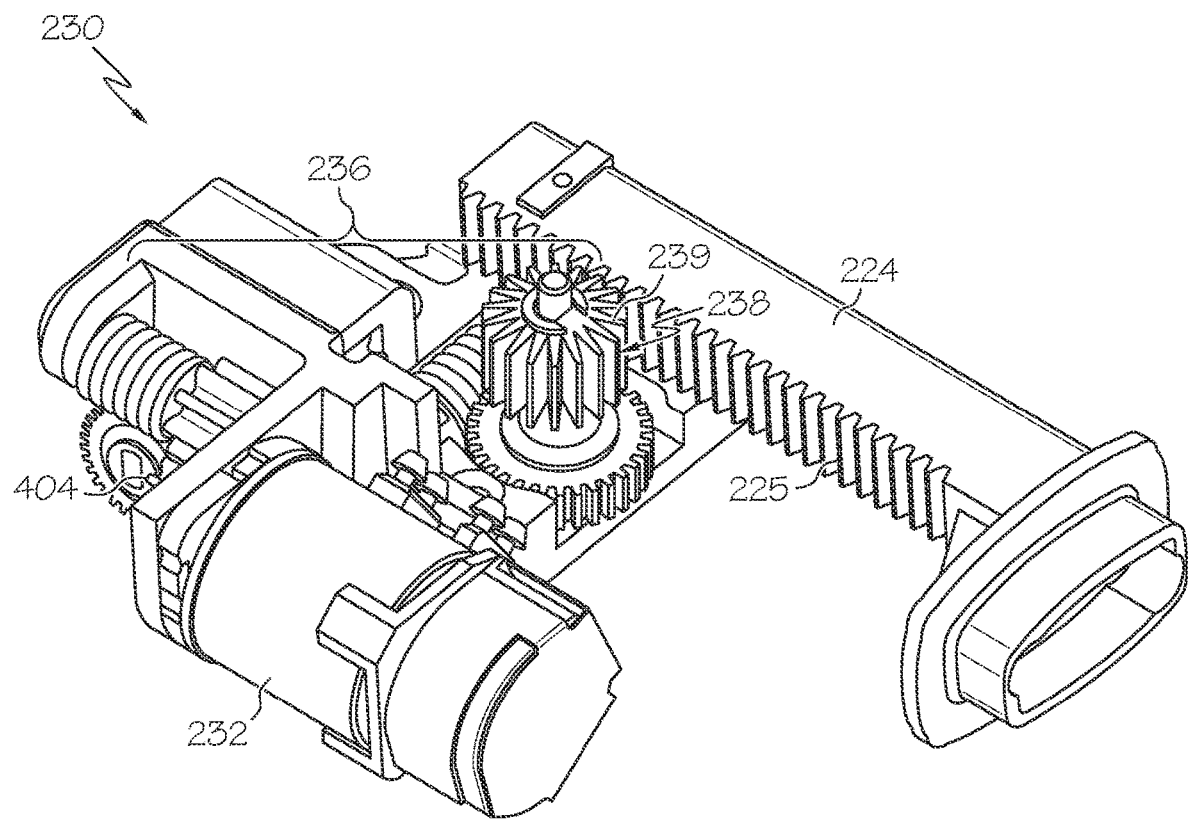
FIG. 6 is a perspective view illustrating the drive system engaged with the shaft of the plunger when the fluid reservoir is seated within the durable housing of FIG. 3.

FIGS. 4-6 depict perspective and cross-sectional views of the drive system 230 provided in the durable housing 202. Various aspects of the motor drive system 230 may be similar to those described in U.S. patent application Ser. No. 13/049,803. The drive system 230 includes a motor 232 having a rotor 530 that is mechanically coupled to a gear assembly 236 that translates rotation of the rotor 530 to translational displacement the plunger 222 in the direction 250 of the fluid delivery port 210 to deliver fluid from the reservoir 206 to a user. Accordingly, the direction 250 may alternatively be referred to herein as the fluid delivery direction 250.

In exemplary embodiments, the motor 232 is realized as a DC motor, such as a stepper motor or brushless DC motor capable of precisely controlling the amount of displacement of the plunger 222 during operation of the infusion device 200. As best illustrated in FIGS. 4-5, in exemplary embodiments, the rotor 530 of the motor 232 is mechanically coupled to a rotary shaft 402, which, in turn, is mechanically coupled to a first gear 404 of the gear assembly 236. In the illustrated embodiment of FIGS. 4-5, the first gear 404 is coaxial and/or concentric to and disposed about the rotary shaft 402, and the first gear 404 is affixed to or otherwise integrated with the rotary shaft 402 such that the first gear 404 and the rotary shaft 402 rotate in unison. The gear assembly 236 also includes a pinion gear 238 having exposed teeth 239 that are configured to mate with or otherwise engage the exposed teeth 225 on the shaft 224 when the reservoir 206 is seated in the durable housing 202, such that rotation or displacement of the pinion gear 238 in rotational delivery direction 350 produces a corresponding translational displacement of the shaft 224 and/or plunger 222 in the fluid delivery direction 250 to deliver fluid to the user.

During operation of the fluid infusion device 200, when the motor 232 is operated to rotate the rotor 530, the rotary shaft 402 rotates in unison with the rotor 530 to cause a corresponding rotation of the first gear 404, which, in turn, actuates the gears of the gear assembly 236 to produce a corresponding rotation or displacement of the pinion gear 238, which, in turn, displaces the shaft 224. In this manner, the rotary shaft 402 translates rotation (or displacement) of the rotor 530 into a corresponding rotation (or displacement) of the gear assembly 236 such that the teeth 239 of the pinion gear 238 apply force to the teeth 225 of the shaft 224 of the plunger 222 in the fluid delivery direction 250 to thereby displace the plunger 222 in the fluid delivery direction 250 and dispense, expel, or otherwise deliver fluid from the barrel 220 of the reservoir 206 to the user via the fluid delivery path provided by the cannula 208.

Referring to FIG. 5, in an exemplary embodiment, a sensor 500 is configured to measure, sense, or otherwise detect rotation (or displacement) of the rotary shaft 402 and/or the rotor 530 of the motor 232. For convenience, but without limitation, the sensor 500 may alternatively be referred to herein as a motor position sensor or rotor position sensor. The sensor 500 may be utilized to provide closed-loop control of the motor 232, such as, for example, as described in U.S. patent application Ser. No. 13/425,174, the subject matter of which is hereby incorporated by reference in its entirety. In exemplary embodiments, the rotary shaft 402 includes a detectable feature that is measurable or otherwise detectable by the motor position sensor 500. In the illustrated embodiment, a rotary member (or wheel) 502 is provided on the rotary shaft 402 and includes a plurality of protruding features (or arms) 504 that are measurable or otherwise detectable by the motor position sensor 500. In the illustrated embodiment, the wheel 502 is coaxial and/or concentric to and disposed about the rotary shaft 402, and the wheel 502 is affixed to or otherwise integrated with the rotary shaft 402 such that the wheel 502 and the rotary shaft 402 rotate in unison. In this manner, rotation (or displacement) of the wheel 502 corresponds to the displacement of the rotary shaft 402 and/or the rotor 530 of the motor 232.

In exemplary embodiments, the sensor 500 is realized as an incremental position sensor configured to measure, sense, or otherwise detect incremental rotations of the rotary shaft 402 and/or the rotor 530 of the motor 232. For example, in accordance with one or more embodiments, the sensor 500 is realized as a rotary encoder. In alternative embodiments, the sensor 500 may be realized using any other suitable sensor, such as (but not limited to) a magnetic sensor, optical sensor (or other light detector), tactile sensor, capacitive sensor, inductive sensor, and/or the like. In exemplary embodiments, the incremental position sensor 500 may be configured to count or otherwise sense incremental rotations of the motor 232 via the wheel 502, for example, by counting each time a protruding feature 504 passes by the sensor 500. In this regard, when the number of protruding features 504 equals or otherwise corresponds to the number of discrete motor steps of the stepper motor 232, the incremental position sensor 500 counts or otherwise senses the number of motor steps traversed by the rotary shaft 402 and/or rotor of the motor 232. In some embodiments, the sensor 500 includes an emitter 510 and a detector 512 disposed on opposite sides of the wheel 502 such that at least a portion of the protruding features 504 passes between the emitter 510 and the detector 512 as the wheel 502 rotates. In this regard, the sensor 500 may detect or otherwise count each instance when a protruding feature 504 interrupts a transmission from the emitter 510 to the detector 512. Alternatively, the sensor 500 may detect or otherwise count each instance a transmission from the emitter 510 to the detector 512 is uninterrupted or otherwise completed (e.g., via gaps between protruding features 504).

Figure 7:
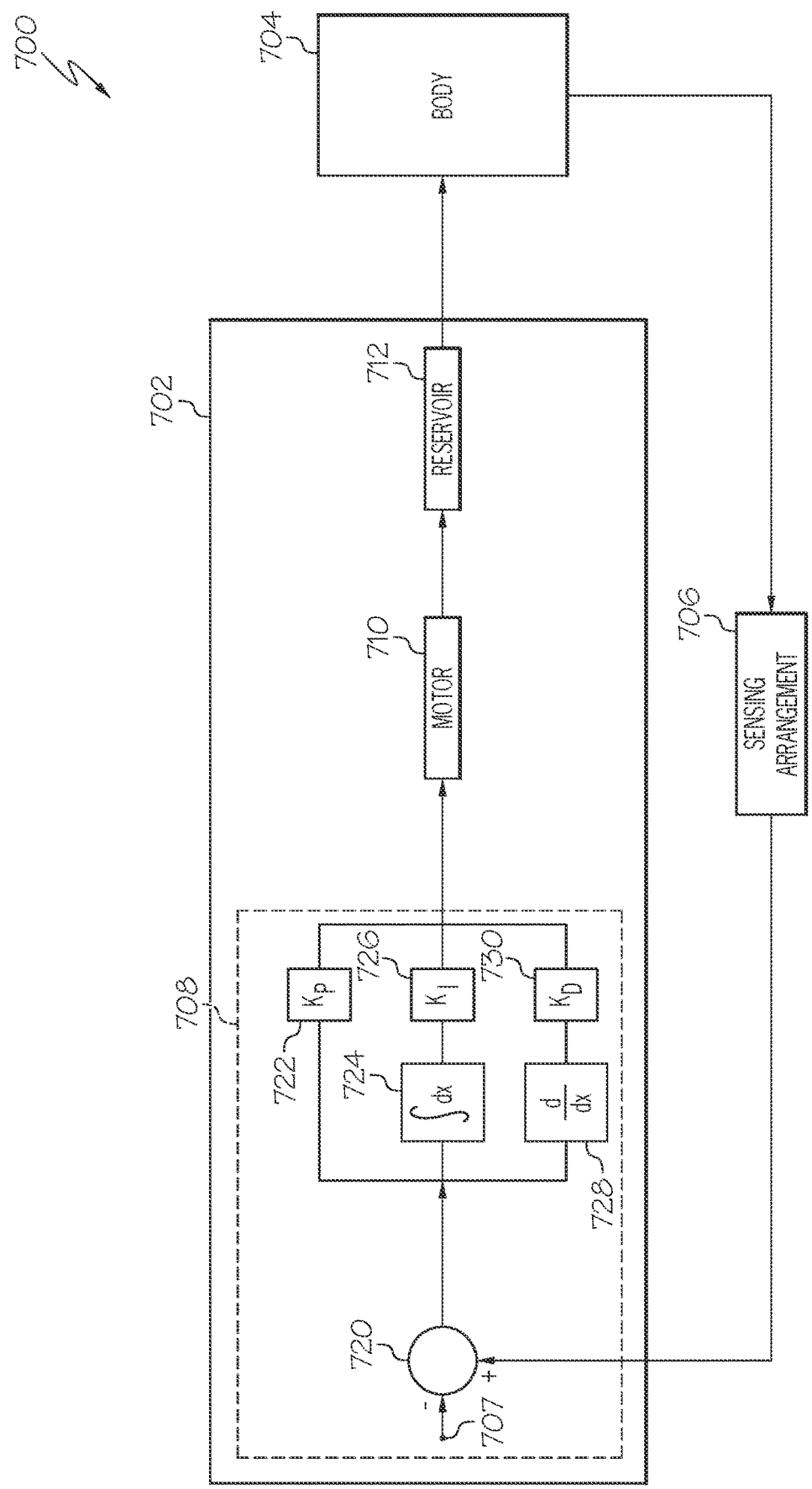
FIG. 7 is a block diagram of a closed-loop control system that may be implemented or otherwise supported by a fluid infusion device in one or more exemplary embodiments.

Referring now to FIG. 7, as described above in the context of FIG. 1, in exemplary embodiments, an infusion device 702 (e.g., infusion device 102, 200) is configured to implement a closed-loop control system 700 that regulates a condition in the body 704 of a user to a desired (or target) value. In one or more exemplary embodiments, the condition being regulated is sensed, detected, measured or otherwise quantified by a sensing arrangement 706 (e.g., sensing arrangement 104) communicatively coupled to the infusion device 702. However, it should be noted that in alternative embodiments, the condition being regulated by the control system 700 may be correlative to the measured values obtained by the sensing arrangement 706. For example, the condition being regulated could be a blood glucose level or another condition that is influenced by physical activity of the user, and the sensing arrangement 706 may be realized as a heart rate monitor, a gyroscope, an accelerometer, or another suitable physiological sensor that provides measured values indicative of the level of physical activity being exhibited by the user. It should be appreciated that FIG. 7 is a simplified representation of the control system 700 for purposes of explanation and is not intended to limit the subject matter described herein in any way. In this regard, more complex control schemes may be implemented by the control system 700 with multiple sensing arrangements 706 being utilized in conjunction with one another. For example, a blood glucose sensing arrangement may be used with a heart rate monitor to implement a control scheme that regulates a user's blood glucose level based on the measured blood glucose level in a manner that accounts for the user's level of physical activity. That said, for clarity and ease of explanation, the subject matter may be described herein in the context of the control system 700 having an individual sensing arrangement 706 that senses, detects, measures or otherwise quantifies the condition being regulated.

In the illustrated embodiment, the infusion device 702 includes a control module 708 coupled to a motor 710 (e.g., motor 232) that is operable to displace a plunger (e.g., plunger 222) in a reservoir 712 (e.g., reservoir 206). Although FIG. 7 depicts the reservoir 712 as residing outside the infusion device 702, in practice, the reservoir 712 will typically be inserted or otherwise provided within the housing of the infusion device 702 during operation of the control system 700 as described above in the context of FIGS. 2-6. As described above, displacement of the plunger results in the delivery of a fluid that is capable of influencing the condition in the body 704 of the user to the body 704 of the user via a fluid delivery path (e.g., via cannula 208). To support closed-loop control, the control module 708 receives or otherwise obtains a desired value (e.g., a target or command value) for the condition in the body 704 of the user at input 707. In exemplary embodiments, the infusion device 702 stores or otherwise maintains the target value (e.g., in a data storage element), however, in some alternative embodiments, the target value may be received from an external component (e.g., CCD 106 and/or computer 108).

The illustrated control module 708 implements or otherwise provides proportional-integral-derivative (PID) control to determine or otherwise generate delivery commands for operating the motor 710 based at least in part on a difference between the desired value and a measured value for that condition in the body 704 obtained from the sensing arrangement 706. In this regard, the PID control attempts to minimize the difference between the measured value and the desired value, and thereby regulates the measured value to the desired value. For example, the control module 708 may apply PID control parameters to the difference between a target blood glucose level at input 707 and a measured blood glucose level in the body 704 received from the sensing arrangement 706 to determine a delivery command. Based on that delivery command, the control module 708 operates the motor 710 to deliver insulin from the reservoir 712 to the body 704 of the user to influence the user's blood glucose level and thereby reduce the difference between a subsequently measured blood glucose level and the target blood glucose level.

Still referring to FIG. 7, the illustrated control module 708 includes or otherwise implements a summation block 720 configured to determine a difference between the target value obtained at input 707 and the measured value obtained from the sensing arrangement 706, for example, by subtracting the target value from the measured value. The output of the summation block 720 represents the difference between the measured and target values that is then provided to each of a proportional term path, an integral term path, and a derivative term path. The proportional term path includes a gain block 722 that multiplies the difference by a proportional gain coefficient, $K_P$, to obtain the proportional term. The integral term path includes an integration block 724 that integrates the difference and a gain block 726 that multiplies the integrated difference by an integral gain coefficient, $K_i$, to obtain the integral term. The derivative term path includes a derivative block 728 that determines the derivative of the difference and a gain block 730 that multiplies the derivative of the difference by a derivative gain coefficient, $K_D$, to obtain the derivative term. The proportional term, the integral term, and the derivative term are then added or otherwise combined to obtain a delivery command that is utilized to operate the motor. Various implementation details pertaining to closed-loop PID control and determine gain coefficients are described in greater detail in U.S. Pat. No. 7,402,153, which is incorporated by reference.

Again, it should be noted that FIG. 7 is a simplified representation of the control system 700 for purposes of explanation and is not intended to limit the subject matter described herein in any way. In this regard, depending on the particular control scheme being implemented, practical embodiments of the control system 700 may include any number of control parameters configured to compensate, correct, or otherwise account for various operating conditions experienced and/or exhibited by the infusion device 702 and/or the sensing arrangement 706, such as, for example, one or more patient-specific control parameters (e.g., an insulin sensitivity factor, a daily insulin requirement, an insulin limit, a reference basal rate, a reference fasting glucose, an active insulin action duration, pharmodynamical time constants, or the like) or one or more of the tuning parameters described in U.S. Pat. No. 7,402,153. In some embodiments, one or more patient-specific control parameters are utilized to calculate or otherwise determine the target value that is provided at input 707 and utilized by the control system 700 to generate delivery commands. For example, a target blood glucose value at the input 707 may be calculated based at least in part on a patient-specific reference basal rate and a patient-specific daily insulin requirement. Although FIG. 7 depicts PID control, the subject matter described herein is not limited to PID control. Additionally, the control system 700 may include components configured to filter or otherwise process the output of the sensing arrangement 706. Accordingly, as used herein, terms such as measured value, measurement data, and the like should be understood as referring to the values and/or signals provided to or otherwise received by the infusion device 702 and/or the control module 708 and are not necessarily identical to an analog output that may be generated by a sensing element of the sensing arrangement 706.

Figure 8:
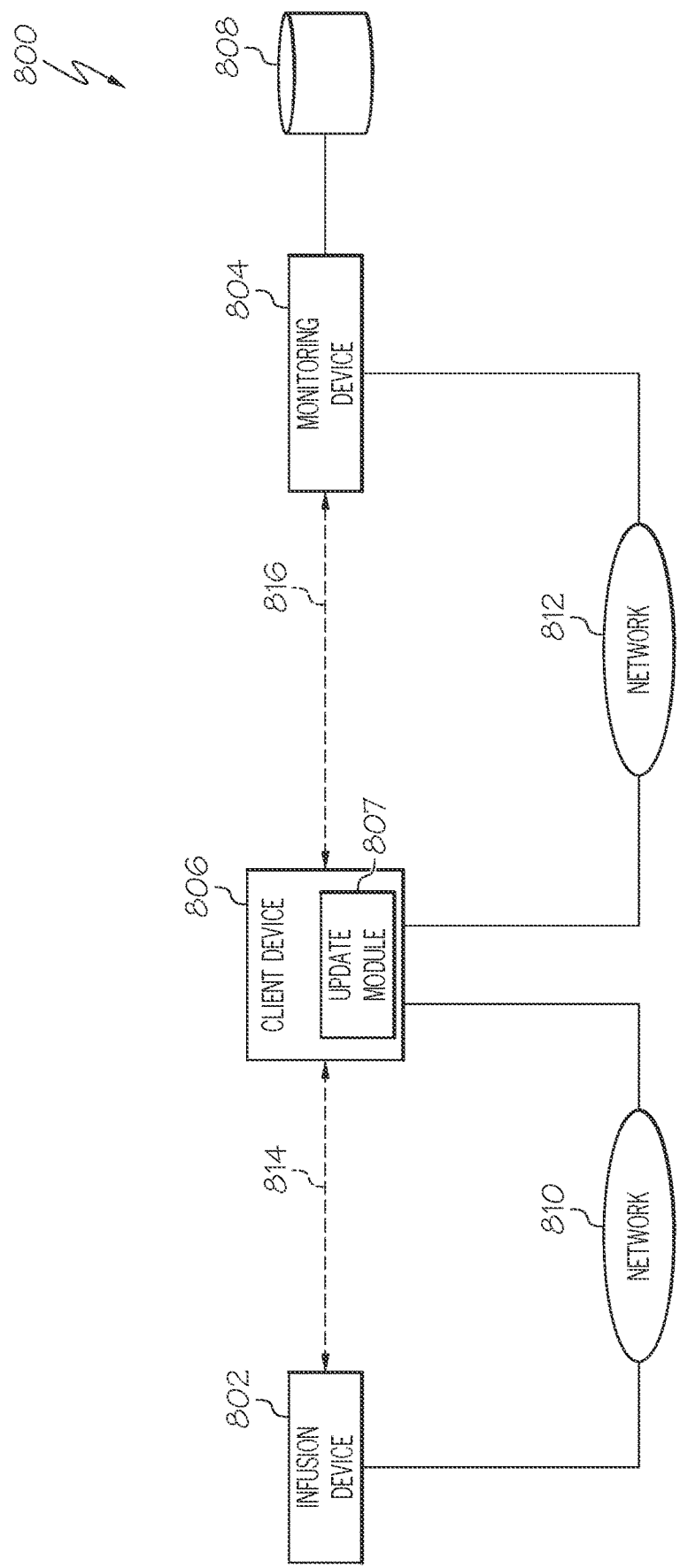
FIG. 8 is a block diagram of an infusion system suitable for use with the fluid infusion device in the closed-loop control system of FIG. 7 to dynamically adjust the closed-loop control system based at least in part on measurement data for a user in accordance with one or more exemplary embodiments.

Referring now to FIG. 8, in one or more exemplary embodiments, an infusion system 800 includes an infusion device 802 (e.g., infusion device 102, 200, 702) that communicates with a remote device 804 via an intermediate device 806. The remote device 804 generally represents a server or another suitable electronic device configured to analyze or otherwise monitor measurement (or sensor) data obtained for the user associated with the infusion device 802 along with delivery data for the infusion device 802 and determine updated control information for operating the infusion device 802 based at least in part on the measurement data and delivery data. For example, the remote device 804 may determine updated gain coefficient values for PID control (e.g., a proportional gain coefficient, an integral gain coefficient, a derivative gain coefficient, or the like) implemented by the infusion device 802 and provide the updated gain coefficient values to the infusion device 802 for use during subsequent deliveries, as described in greater detail below. For purposes of explanation, but without limitation, the remote device 804 may alternatively be referred to herein as a monitoring device or a monitoring server. In practice, the monitoring device 804 may reside at a location that is physically distinct and/or separate from the infusion device 802, such as, for example, at a facility that is owned and/or operated by or otherwise affiliated with a manufacturer of the infusion device 802.

As described in greater detail below, in exemplary embodiments, the infusion device 802 periodically and/or autonomously uploads measurement data indicative of a particular condition of its associated user to the monitoring device 804 via the intermediate device 806. For example, the infusion device 802 may periodically upload measured blood glucose values obtained from a sensing arrangement (e.g., sensing arrangement 104, 706) to the monitoring device 804 via the intermediate device 806. In exemplary embodiments, the monitoring device 804 is coupled to a database 808 or another suitable data storage element, and the monitoring device 804 stores or otherwise maintains the measurement data in the database 808 in association with the infusion device 802 and/or its associated user. For example, the monitoring device 804 may utilize a unique identifier associated with the infusion device 802 and/or a unique identifier associated with the user to which the infusion device 802 belongs to maintain measurement data obtained from that infusion device 802 in association with the appropriate user. Along with the measurement data, the infusion device 802 may also periodically and/or autonomously upload delivery data indicative of the amount of fluid delivered by the infusion device (e.g., delivery commands), the timing of the fluid delivery (e.g., date and/or time of day a delivery command was executed), and/or other information that characterizes or otherwise quantifies the delivery of fluid by the infusion device 802. In such embodiments, the monitoring device 804 stores or otherwise maintains the delivery data in the database 808 in association with the measurement data, the infusion device 802 and/or its associated user (e.g., using the unique identifier associated with the infusion device 802 and/or the unique identifier associated with the user to which the infusion device 802 belongs.

The monitoring device 804 analyzes the user's measurement data and/or the delivery data for the infusion device 802 that is stored in the database 808 to determine whether one or more control parameters or other control information for the infusion device 802 should be updated, modified, or otherwise adjusted. In exemplary embodiments, the monitoring device 804 autonomously and automatically analyzes the user's stored measurement data and/or delivery data in the database 808 on a periodic basis (e.g., daily or every 24 hours) to update, modify, or otherwise adjust one or more control parameters or other control information for the infusion device 802. For example, the monitoring device 804 may periodically analyze the measurement data and delivery data to calculate or otherwise determine an updated daily insulin requirement for the user by averaging the amount of insulin delivered by the infusion device 802 and adjust one or more of the PID gain coefficients and/or a target value for a PID control loop based on the updated daily insulin requirement. Additionally, using the updated daily insulin requirement, the stored measurement data from the most recent 24-hour period along with stored measurement data from preceding 24-hour intervals (or days) along with the delivery data for the infusion device 802 during those intervals, the monitoring device 804 may determine updated values for one or more patient-specific control parameters (e.g., an insulin sensitivity factor, a daily insulin requirement, an insulin limit, a reference basal rate, a reference fasting glucose, an active insulin action duration, pharmodynamical time constants, or the like). In various embodiments, the monitoring device 804 may perform regression analysis, curve fitting, or some other mathematical techniques to adjust or otherwise optimize the control parameters and/or target values. Depending on the embodiment, a subset of the control parameters implemented by the infusion device 802 may be automatically updated on the periodic basis while another subset of control parameters implemented by the infusion device 802 may only updated when the updated values determined by the monitoring device 804 deviate from the current values being implemented by the infusion device 802 by more than some threshold amount (e.g., when a difference between the updated control parameter value and the current control parameter value utilized by the infusion device 802 exceeds a threshold percentage of the current control parameter value). When the monitoring device 804 determines that one or more control parameters should be adjusted or otherwise updated, the monitoring device 804 determines updated values for those control parameters and autonomously provides those updated control parameter values to the infusion device 802 via the intermediate device 806, as described in greater detail below.

In response to receiving updated control information, the infusion device 802 updates the corresponding components of the closed-loop control loop to implement the updated control information (e.g., by changing the coefficients used by one or more of the gain blocks 722, 726, 730). Thereafter, the infusion device 802 operates in accordance with the updated control information, such that the updated control information influences subsequent deliveries of fluid to the user, and thereby influences subsequent measurement data for the user. In a similar manner as described above, the infusion device 802 may periodically and/or autonomously upload the subsequent measurement data and/or delivery data to the monitoring device 804, which, in turn, stores and analyzes the subsequent measurement data and/or delivery data to determine whether the control parameters should be adjusted further. In this manner, the infusion device 802 and the monitoring device 804 are cooperatively configured to dynamically adjust the control information for operating the infusion device 802 based on that user's recent measurement data and/or delivery data to accommodate lifestyle changes by that user and/or changes to that user's individual needs.

In the embodiment of FIG. 8, the intermediate device 806 represents an electronic device capable of communicating with the infusion device 802 via a first communications network 810 and with the monitoring device 804 via a second communications network 812. In this regard, the first network 810 may be physically and/or logically distinct from the second network 812. For example, in accordance with one embodiment, the first network 810 is realized as a Bluetooth network, a ZigBee network, or another suitable personal area network and the second network 812 is realized as a cellular network, a local area network (LAN), a wireless local area network (WLAN), a wide area network (WAN), the Internet, or the like. Depending on the embodiment, the intermediate device 806 may be realized as any sort of electronic device capable of communicating over networks 810, 812, such as a mobile telephone, a laptop or notebook computer, a tablet computer, a desktop computer, a personal digital assistant, or the like. For purposes of explanation, but without limitation, the intermediate device 806 may alternatively be referred to herein as a client device. In exemplary embodiments, the client device 806 includes or otherwise implements an update module 807 that supports establishing peer-to-peer communication sessions 814, 816 on the networks 810, 812 and streaming data and/or information between the infusion device 802 and the monitoring device 804 via the peer-to-peer communication sessions 814, 816. In this regard, the update module 807 generally represents a software module or another feature that is generated or otherwise implemented by the client device 806 to support the updating and monitoring processes described herein. In one or more exemplary embodiments, the update module 807 is configured to store or otherwise maintain an address and/or other identification information for the monitoring device 804 on the second network 812.

In exemplary embodiments, the infusion device 802 and the client device 806 establish an association (or pairing) with one another over the first network 810 to support subsequently establishing a peer-to-peer communication session 814 between the infusion device 802 and the client device 806 via the first network 810. For example, in accordance with one embodiment, the first network 810 is realized as a Bluetooth network, wherein the infusion device 802 and the client device 806 are paired with one another (e.g., by obtaining and storing network identification information for one another) by performing a discovery procedure or another suitable pairing procedure. In this regard, the pairing information obtained during the discovery procedure allows either of the infusion device 802 or the client device 806 to initiate the establishment of a secure peer-to-peer communication session 814 via the first network 810.

Additionally, the monitoring device 804 establishes an association between the client device 806 and its paired infusion device 802 and/or associated user to support establishing another peer-to-peer communication session 816 between the client device 806 and the monitoring device 804 via the second network 812. For example, after the client device 806 is paired with the infusion device 802, the update module 807 may automatically operate the client device 806 to contact the monitoring device 804 via the second network 812 and provide network identification information for the client device 806 on the second network 812 along with an indication of its paired infusion device 802 and/or associated user. Alternatively, the user may manipulate or otherwise operate the client device 806 and/or update module 807 to contact the monitoring device 804 via the second network 812 and provide the identification information. The monitoring device 804 stores or otherwise maintains the network identification information for the client device 806 in the database 808 in association with the infusion device 802 and/or its associated user to allow either of the monitoring device 804 or the client device 806 to initiate the establishment of a secure peer-to-peer communication session 816 via the second network 812.

As described in greater detail below in the context of FIGS. 11-13, to upload measurement data to the monitoring device 804, the infusion device 802 autonomously attempts to initiate the peer-to-peer communication session 814 with the client device 806 over the first network 810. In response to a connection request from the infusion device 802, the client device 806 and/or update module 807 automatically attempts to initiate the peer-to-peer communication session 816 with the monitoring device 804 over the second network 812. In response to receiving an acknowledgement from the monitoring device 804 that establishes the peer-to-peer communication session 816, the client device 806 and/or update module 807 automatically provides an acknowledgment to the infusion device 802 that establishes the peer-to-peer communication session 814. In response to receiving the acknowledgment, the infusion device 802 automatically transmits the measurement data via the peer-to-peer communication session 814 over the first network 810 to the client device 806 and/or update module 807, which, in turn, automatically retransmits the measurement data via the peer-to-peer communication session 816 over the second network 812 to the monitoring device 804. In this regard, the measurement data is not stored on the client device 806, other than whatever temporary storing or buffering may be required to prevent loss of data while receiving and retransmitting the measurement data. Thus, the measurement data is effectively streamed to the monitoring device 804 through the client device 806. In exemplary embodiments, the infusion device 802 autonomously terminates the peer-to-peer communication session 814 after transmitting the measurement data to the client device 806 and/or update module 807, which, in turn, automatically terminates the peer-to-peer communication session 816 after retransmitting the measurement data to the monitoring device 804.

In a similar manner, to communicate updated control parameters to the infusion device 802, the monitoring device 804 autonomously attempts to initiate the peer-to-peer communication session 816 with the client device 806 over the second network 812. In response to the connection request, the client device 806 and/or update module 807 automatically attempts to initiate the peer-to-peer communication session 814 with the infusion device 802 over the first network 810. In response to receiving an acknowledgement that establishes the peer-to-peer communication session 814, the client device 806 and/or update module 807 automatically provides an acknowledgment to the monitoring device 804 that establishes the peer-to-peer communication session 816. In response to receiving the acknowledgment, the monitoring device 804 automatically transmits the updated control parameter values via the peer-to-peer communication session 816 over the second network 812 to the client device 806 and/or update module 807, which, in turn, automatically transmits the updated control parameter values via the peer-to-peer communication session 814 over the first network 810 to the infusion device 802. In this regard, in exemplary embodiments, the updated control parameter values are not stored on the client device 806, other than whatever temporary storing or buffering may be required to prevent loss of data while receiving and re-transmitting the updated control parameter values. In exemplary embodiments, the monitoring device 804 terminates the peer-to-peer communication session 816 after transmitting the updated control parameter values to the client device 806 and/or update module 807, which, in turn, terminates the peer-to-peer communication session 814 after re-transmitting the updated control parameter values to the infusion device 802.

Figure 9:
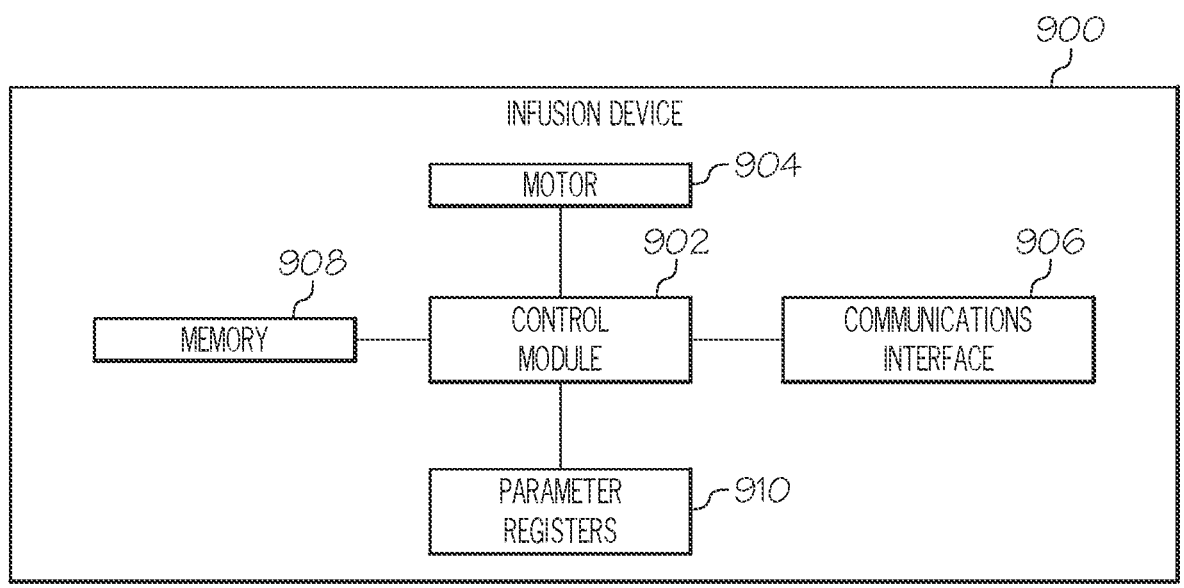
FIG. 9 is a block diagram of an infusion device suitable for use in the infusion system of FIG. 8 in accordance with one or more exemplary embodiments.

FIG. 9 depicts a block diagram of an exemplary embodiment of an infusion device 900 suitable for use as the infusion device 702 in the control system 700 of FIG. 7 and/or the infusion device 802 in the infusion system 800 of FIG. 8. The illustrated infusion device 900 includes, without limitation, a control module 902, a motor 904, a communications interface 906, and data storage elements 908, 910. As described above in the context of FIG. 2, the motor 904 is operable to displace a plunger (e.g., plunger 222) of a reservoir (e.g., reservoir 206) inserted in or otherwise provided to the infusion device 900, and thereby deliver fluid to the user wearing the infusion device 900.

The control module 902 generally represents the hardware, circuitry, logic, firmware and/or other components of the infusion device 900 configured to determine delivery commands for operating the motor 904 using closed-loop control and perform various additional tasks, operations, functions and/or operations described herein. Depending on the embodiment, the control module 902 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 902, or in any practical combination thereof. In exemplary embodiments, the motor control module 902 includes or otherwise accesses a data storage element or memory 908, including any sort of random access memory (RAM), read only memory (ROM), flash memory, registers, hard disks, removable disks, magnetic or optical mass storage, short or long term storage media, or any other non-transitory computer-readable medium capable of storing programming instructions for execution by the control module 902. The computer-executable programming instructions, when read and executed by the control module 902, cause the control module 902 to perform the tasks, operations, functions, and processes described in greater detail below. In this regard, the control scheme or algorithm implemented by the control module 902 may be realized as control application code that is stored or otherwise maintained in the memory 908 and executed by the control module 902 to implement or otherwise provide the closed-loop PID control components (e.g., blocks 720, 722, 724, 726, 728, 730) in software.

Still referring to FIG. 9, and with reference to FIG. 7, in exemplary embodiments, the control module 902 obtains a target value for a condition of the user associated with the infusion device 900, obtains a measured (or sensed) value for the condition from a sensing arrangement (e.g., sensing arrangement 706), and performs PID control to regulate the measured value to the target value. In this regard, the control module 902 includes or otherwise implements a summation block that determines a difference between the target value and the measured value, a proportional gain block that multiplies the difference by a proportional gain coefficient, integration and gain blocks that multiply the integrated difference by an integration gain coefficient, and derivative and gain blocks that multiply the derivative of the difference by a derivative gain coefficient.

In the illustrated embodiment of FIG. 9, the data storage element 910 generally represents the hardware, circuitry and/or other components of the infusion device 900 configured to store the control parameters for the control scheme implemented by the control module 902. The data storage element 910 may be realized as any sort of random access memory (RAM), read only memory (ROM), flash memory, registers, hard disks, removable disks, magnetic or optical mass storage, short or long term storage media, or any other non-transitory computer-readable medium. That said, in exemplary embodiments, the data storage element 910 is realized a plurality of registers associated with the control parameters for the PID control, and accordingly, the data storage element 910 may alternatively be referred to herein as the parameter registers. For example, a first register of the parameter registers 910 may be accessed by or otherwise coupled to the summation block (e.g., at input 707 to summation block 720) and store the target value for the condition being regulated. A second register of the parameter registers 910 may be accessed by or otherwise coupled to the proportional gain block (e.g., proportional gain block 722) and store the proportional gain coefficient used by the proportional gain block to multiply the difference value. Similarly, a third register of the parameter registers 910 may be accessed by or otherwise coupled to the integration gain block (e.g., integration gain block 726) and store the integration gain coefficient that the integrated difference value is multiplied by, and a fourth register of the parameter registers 910 may be accessed by or otherwise coupled to the derivative gain block (e.g., derivative gain block 730) and store the derivative gain coefficient that the derivative of the difference is multiplied by.

Still referring to FIG. 9, the communications interface 906 generally represents the hardware, circuitry, logic, firmware and/or other components of the infusion device 900 configured to support communications to/from the infusion device 900. The communications interface 906 may include or otherwise be coupled to one or more transceiver modules capable of supporting wireless communications between the infusion device 900 and a client device over a network (e.g., client device 806 via network 810) and/or wireless communications between the infusion device 900 and the sensing arrangement on the body of the user. For example, the first network 810 may be realized as a Bluetooth network, wherein the communications interface 906 includes or is coupled to a Bluetooth adapter capable of establishing the peer-to-peer communication session 814 over the first network 810 in accordance with the Bluetooth specification.

Referring to FIG. 8 and with continued reference to FIG. 9, in exemplary embodiments, the transceiver module associated with the communications interface 906 that is utilized for communicating with the client device 806 over the first network 810 is operated in a low power mode (e.g., a sleep mode, an idle mode, or the like) whenever the peer-to-peer communication session 814 is terminated or otherwise not required for communicating data and/or information. In this regard, the control module 902 may wake or otherwise transition the transceiver module from the low power mode to an active mode to transmit measurement data and/or receive control parameter values before transitioning the transceiver module back to the low power mode once the peer-to-peer communication session 814 is terminated.

It should be understood that FIG. 9 is a simplified representation of an infusion device 900 for purposes of explanation and is not intended to limit the subject matter described herein in any way. In this regard, although FIG. 9 depicts the data storage elements 908, 910 as being distinct or otherwise separate from one another, in practice, the data storage elements 908, 910 may be realized using a single integrated data storage element. Furthermore, although FIG. 9 depicts the communications interface 906 as residing within the infusion device 900 (e.g., within housing 202), in alternative embodiments, the transceiver modules and/or other components of the communications interface 906 may not reside within the housing of the infusion device 900. For example, the communications interface 906 may be realized as a port that is adapted to receive or otherwise be coupled to a wireless adapter that includes one or more transceiver modules and/or other components that support the operations of the infusion device 900 described herein.

Figure 10:
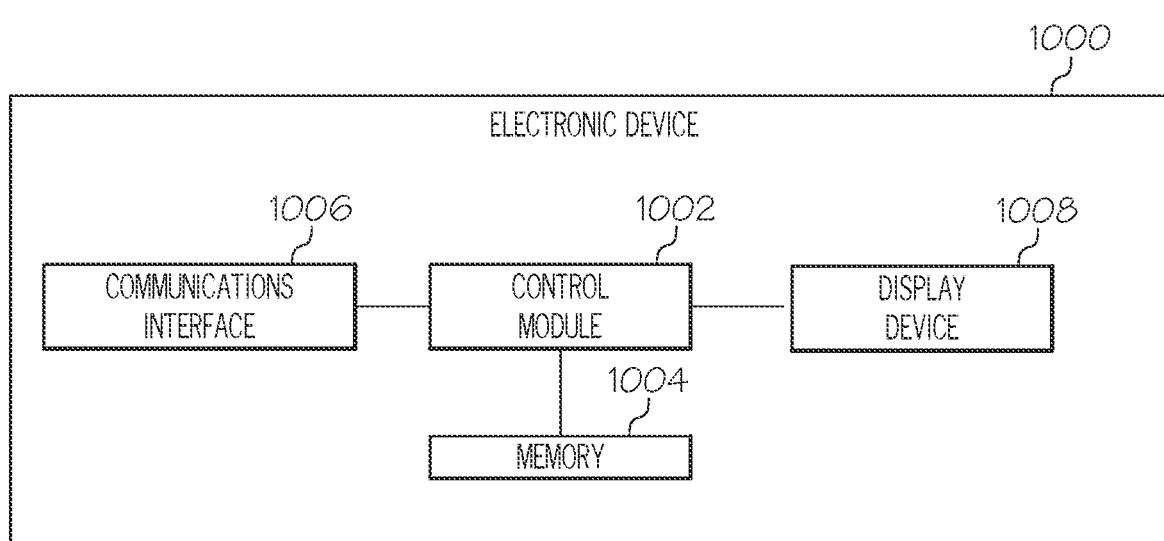
FIG. 10 is a block diagram of an electronic device suitable use in the infusion system of FIG. 8 in accordance with one or more exemplary embodiments.

FIG. 10 depicts a block diagram of an exemplary embodiment of an electronic device 1000 suitable for use as the monitoring device 804 or the client device 806 in the infusion system 800 of FIG. 8. The illustrated electronic device 1000 includes, without limitation, a control module 1002, a data storage element or memory 1004, a communications interface 1006, and a display device 1008. It should be understood that FIG. 10 is a simplified representation of the electronic device 1000 for purposes of explanation and ease of description, and FIG. 10 is not intended to limit the subject matter in any way.

The control module 1002 generally represents the hardware, circuitry, logic, firmware and/or other components of the electronic device 1000 configured to perform the various tasks, operations, functions and/or operations described herein and support the updating and monitoring processes described herein in connection with the infusion system 800 of FIG. 8. Depending on the embodiment, the control module 1002 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 1002, or in any practical combination thereof. In this regard, the memory 1004 represents any non-transitory short or long term storage media capable of storing programming instructions for execution by the control module 1002, which, when read and executed by the control module 1002, cause the control module 1002 to perform certain tasks, operations, functions, and processes described herein.

In the illustrated embodiment, the communications interface 1006 generally represents the hardware, software, firmware and/or combination thereof that is coupled to the control module 1002 and cooperatively configured to support communications to/from the electronic device 1000 via a network in a conventional manner. In this regard, when the electronic device 1000 is realized as the client device 806, the communications arrangement may include a first transceiver module configured to support communications on the first network 810 and a second transceiver module configured to support communications on the second network 812.

The display device 1008 is realized as an electronic display (e.g., a liquid crystal display (LCD), a light emitting diode (LED) display, or the like) configured to graphically display data and/or information under control of the control module 1002. For example, the user associated with the infusion device 802 may manipulate the client device 806 in a manner that causes the control module 1002 to generate, on the display device 1008, one or more graphical representations associated with the condition of the user being regulated by the infusion device 802, such as, for example, a current glucose level of the user, a graph or chart of the user's glucose level versus time, device status indicators, alert messages, or the like. In some embodiments, the user associated with the infusion device 802 may manipulate the client device 806 in a manner that causes the control module 1002 to contact the monitoring device 804 for a graphical representation of the stored measurement data maintained in the database 808. For example, the monitoring device 804 may generate a graph of the user's historical daily average insulin concentration profile and provide the graph to the client device 806 for presentation on the display 1008. In other embodiments, the control module 1002 may present, on the display 1008, graphical user interface (GUI) elements adapted to allow the user to modify one or more aspects of his or her treatment. For example, a user may modify a target value utilized by the infusion device 802 to generate delivery commands or modify the reference (or target) insulin profiles used by the monitoring device 804 to determine control information for the infusion device 802.

Figure 11:
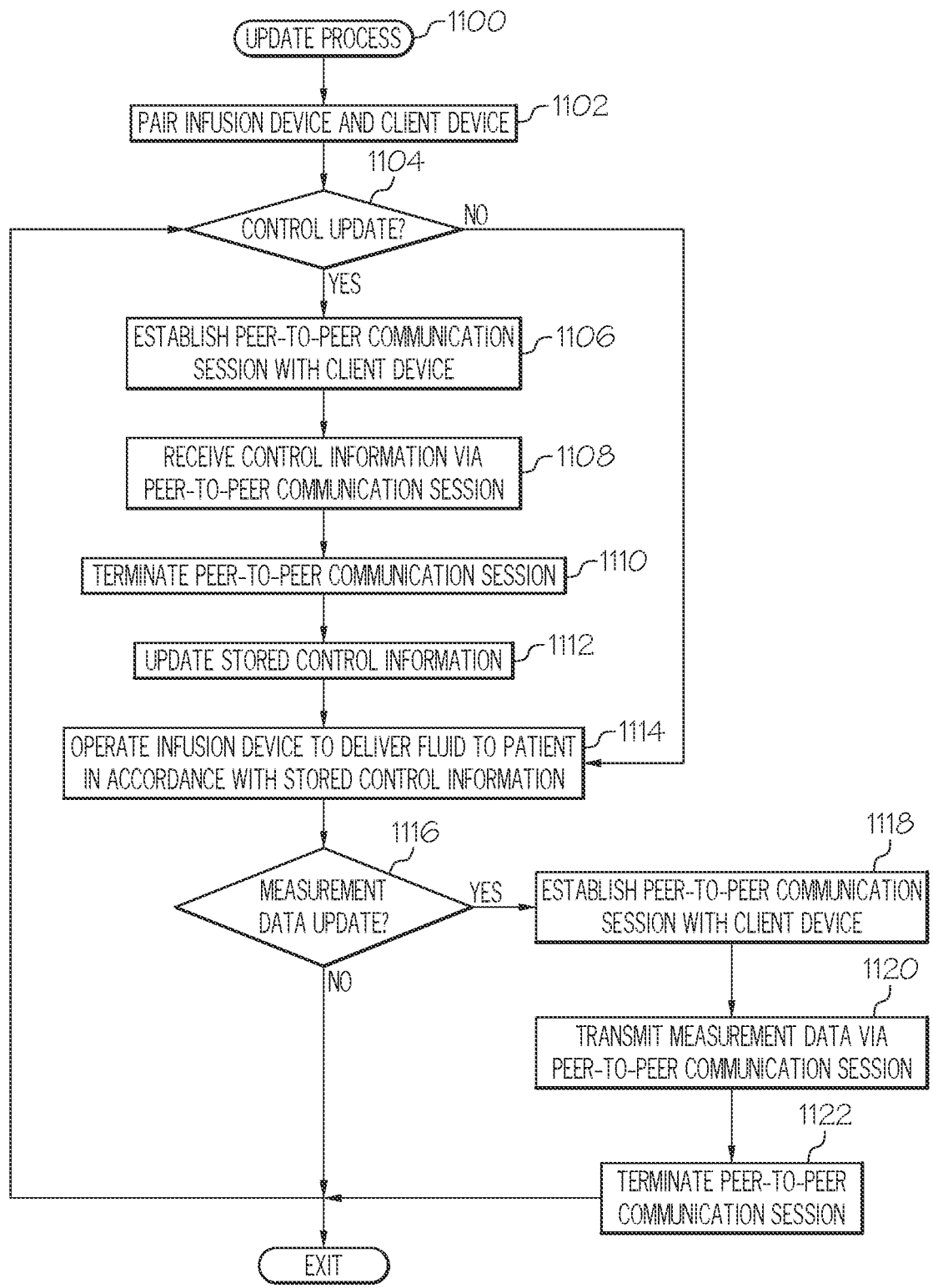
FIG. 11 is a flow diagram of an exemplary update process suitable for use with the infusion system of FIG. 8 to dynamically adjust the closed-loop control system in accordance with one or more exemplary embodiments.

FIG. 11 depicts an exemplary update process 1100 suitable for implementation by a fluid infusion device in an infusion system to dynamically adjust a control scheme being implemented by the fluid infusion device. The various tasks performed in connection with the update process 1100 may be performed by hardware, firmware, software, or any combination thereof. For illustrative purposes, the following description refers to elements mentioned above in connection with FIGS. 1-10. In practice, portions of the update process 1100 may be performed by different elements of an infusion device 702, 802, 900, such as, for example, the control module 708, 902, the motor 710, 904, the communications interface 906, the memory 908 and/or the parameter registers 910. It should be appreciated that the update process 1100 may include any number of additional or alternative tasks, the tasks need not be performed in the illustrated order and/or the tasks may be performed concurrently, and/or the update process 1100 may be incorporated into a more comprehensive procedure or process having additional functionality not described in detail herein. Moreover, one or more of the tasks shown and described in the context of FIG. 11 could be omitted from a practical embodiment of the update process 1100 as long as the intended overall functionality remains intact.

The illustrated process 1100 initializes or otherwise begins by pairing a fluid infusion device with an electronic device that will function as an intermediary for communications between the fluid infusion device and a monitoring device (task 1102). In this regard, the infusion device 702, 802, 900 establishes an association with the client device 806 that is subsequently utilized to establish, create, or otherwise support the peer-to-peer communication session 814. For example, the user may manipulate the infusion device 802, 900 in a manner that causes the control module 902 to enable or otherwise operate a transceiver module associated with the communications interface 906 such that the infusion device 802, 900 is discoverable on the first network 810 or is otherwise capable of discovering the client device 806 on the first network 810. Additionally, the user manipulates the client device 806 to initiate the update module 807 and enable or otherwise operate a transceiver module of the client device 806 such that the client device 806 is discoverable on the first network 810 or is otherwise capable of discovering the infusion device 802 on the first network 810.

In response to detecting the client device 806 on the first network 810, the infusion device 802, 900 and/or control module 902 obtains network identification information for the client device 806 and stores the network identification information (e.g., in memory 908). In this regard, the network identification information may be utilized to uniquely identify and/or authenticate the client device 806 on the first network 810. For example, the network identification information for the client device 806 may include an address of the client device 806 on the first network 810, a unique identifier associated with the transceiver module or another hardware component of the client device 806 used to access the first network 810 (e.g., a Bluetooth address, a media access control address, or the like), and/or the like. In some embodiments, the infusion device 802, 900 may also obtain identification information for the client device 806 on the second network 812, such as a unique identifier associated with the client device 806 (e.g., a mobile phone number, an international mobile station equipment identity number, or the like).

The client device 806 also obtains network identification information that may be utilized to uniquely identify and/or authenticate the infusion device 802, 900 on the first network 810 and stores the obtained network identification information. For example, the network identification information for the infusion device 802, 900 may include an address of the infusion device 802, 900 on the first network 810, and/or the like. In exemplary embodiments, the infusion device 802, 900 may also be configured to provide a unique identifier associated with the infusion device 802, 900 (e.g., a pump ID number) and/or a unique identifier associated with the user (e.g., a user ID number) that may be used by the monitoring device 804 to maintain an association between the client device 806, the infusion device 802, 900, and/or the user wearing the infusion device 802, 900.

As described in greater detail below in the context of FIGS. 12-13, in accordance with one or more embodiments, in response to pairing the client device 806 with the infusion device 802, 900, the update module 807 automatically communicates with the monitoring device 804 to establish the association between the client device 806, the infusion device 802, 900, and/or the user wearing the infusion device 802, 900. For example, the client device 806 may automatically initiate or otherwise establish a peer-to-peer communication session 816 with the monitoring device 804 over the second network 812 and provide the monitoring device 804 with the unique identifier(s) associated with the infusion device 802, 900 and/or the user wearing the infusion device 802, 900 along with identification information for the client device 806 on the second network 812. The monitoring device 804 stores the network identification information for the client device 806 in the database 808 in association with the unique identifier(s) associated with the infusion device 802, 900 and/or the user wearing the infusion device 802, 900.

Still referring to FIG. 11, the update process 1100 continues by identifying whether the control information maintained by the fluid infusion device should be updated or otherwise downloaded (task 1104). In this regard, the infusion device 802, 900 identifies that its control information (e.g., the control application code maintained in memory 908 and/or the control parameters maintained in the parameter registers 910) should be updated in response to receiving an indication from the client device 806. For example, in some embodiments, the infusion device 802, 900 may be initialized without control application code or corresponding control parameters. Accordingly, the monitoring device 804 may identify the infusion device 802, 900 is a newly deployed infusion device upon establishing the association between the client device 806 and the infusion device 802, 900, and provide an indication or notification to the client device 806 to attempt to establish the peer-to-peer communication session 814. In other embodiments, the infusion device 802, 900 may be preloaded with control application code in memory 908 and control parameters in the parameter registers 910. The monitoring device 804 also analyzes or otherwise monitors measurement data obtained from the infusion device 802, 900 to determine whether to update the control application code and/or the control parameters maintained by the infusion device 802, 900 based on the measurement data, and provides an indication or notification to the client device 806 to attempt to establish the peer-to-peer communication session 814. In yet other embodiments, the monitoring device 804 may provide an indication or notification to the client device 806 to attempt to establish the peer-to-peer communication session 814 when a new version of the control application code is published or otherwise released by the manufacturer of the infusion device 802, 900.

In response to receiving an indication of an update to the control information, the update process 1100 continues by establishing a peer-to-peer communication session with the paired client device (task 1106). In this regard, the client device 806 automatically transmits or otherwise provides an indication or notification of a desire to establish the peer-to-peer communication session 814 (e.g., a connection request) to the infusion device 802, 900 via the first network 810 in response to receiving an indication or notification from the monitoring device 804. In response to receiving the indication from the client device 806, the infusion device 802, 900 automatically transmits or otherwise provides a response or acknowledgement to the client device 806 via the first network 810 that establishes or otherwise creates the peer-to-peer communication session 814. In response to the peer-to-peer communication session 814 being established, the client device 806 and/or update module 807 automatically transmits or otherwise provides, to the monitoring device 804 via the network 812, a response to the indication or notification previously received from the monitoring device 804 that establishes or otherwise creates the peer-to-peer communication session 816.

After establishing the peer-to-peer communication session with the client device, the update process 1100 continues by receiving the control information determined by the monitoring device from the client device via the peer-to-peer communication session (task 1108). In this regard, in response to the peer-to-peer communication session 816 being established, the monitoring device 804 automatically transmits or otherwise provides the control information intended for the infusion device 802, 900 to the client device 806 and/or update module 807 via the peer-to-peer communication session 816 over the network 812. The client device 806 and/or update module 807 automatically retransmits, streams, or otherwise forwards the control information received from the monitoring device 804 to the infusion device 802, 900 via the peer-to-peer communication session 814 over the first network 810. In this manner, the infusion device 802, 900 receives or otherwise obtains the control information via the peer-to-peer communication session 814.

Once the updated control information is received by the infusion device, the update process 1100 continues by terminating the peer-to-peer communication session with the client device (task 1110). In one or more embodiments, the client device 806 and/or update module 807 may identify or otherwise determine when all of the control information received from the monitoring device 804 has been transmitted to the infusion device 802, 900. For example, the monitoring device 804 may automatically indicate a desire to terminate the peer-to-peer communication session 816 after transmitting all of the control information intended for the infusion device 802, 900. Thereafter, the client device 806 and/or update module 807 identifies that the peer-to-peer communication session 814 can be terminated in response to termination of the peer-to-peer communication session 816 when all of the control information has been transmitted to the infusion device 802, 900. In some embodiments, the client device 806 and/or update module 807 may also request a confirmation from the infusion device 802, 900 that the entirety of the control information has been received. In response to determining that the peer-to-peer communication session 814 can be terminated, the client device 806 and/or update module 807 may automatically transmit or otherwise provide an indication or notification to terminate the peer-to-peer communication session 814 (e.g., a disconnection request) to the infusion device 802, 900 via the first network 810. In response to receiving the indication, the infusion device 802, 900 automatically terminates the peer-to-peer communication session 814. In exemplary embodiments, the control module 902 automatically transitions the transceiver module of the communications interface 906 that is utilized for receiving the control information from the active mode to a low power mode (e.g., a sleep mode, an idle mode, or the like), thereby terminating the peer-to-peer communication session 814.

Still referring to FIG. 11, the update process 1100 continues by updating the stored control information maintained by the infusion device with the received control information (task 1112). In this regard, the infusion device 802, 900 stores the received control information and may overwrite any previously stored control information. In some embodiments, the infusion device 802, 900 overwrites any previously stored values for one or more control parameters when the received control information includes values for those control parameters. For example, if the received control information includes updated values for one or more gain coefficients to be applied by one or more gain blocks 722, 726, 730 in a control loop, the control module 902 may store those updated values to the corresponding parameter registers 910, thereby overwriting any previously stored gain coefficient values. In this regard, if the received control information includes an updated proportional gain coefficient value, the control module 902 may store the updated proportional gain coefficient value in the proportional gain parameter register 910 that is referenced by the proportional gain block 722. In some embodiments, the received control information may also include an updated target value for the condition of the user (e.g., a change in the basal insulin level) or one or more patient-specific control parameters utilized by the infusion device 802, 900 to calculate the updated target value, wherein the updated target value is stored in the target parameter register 910 referenced by the input 707 and/or summation block 720 of the closed-loop control. In other embodiments, when the received control information includes an update to the control scheme or algorithm implemented by the control module 902, the control module 902 may store the received control application code in the memory 908. In this regard, for updates to a previous control scheme or algorithm, the application code received from the monitoring device 804 may be stored in the memory 908 in a manner that incorporates the received application code with the previously stored application code. Alternatively, for a new control scheme or algorithm, the control module 902 may overwrite the stored application code in memory 908 with the updated application code received from the monitoring device 804.

After the control information maintained by the infusion device is updated, the update process 1100 continues by operating the infusion device to deliver fluid to the user and regulate a condition of the user in accordance with the updated control information (task 1114). In exemplary embodiments, when closed-loop control of the infusion device 702, 802, 900 is enabled, the control module 708, 902 executes or otherwise implements the control application code maintained in the memory 908 to provide closed-loop PID control of the condition of its associated user in accordance with the control parameter values maintained in the parameter registers 910. In this regard, the control module 708, 902 obtains a measured value for the condition of the user from sensing arrangement 706, obtains the target value for the condition from the target parameter register 910, and determines the difference between the measured value and the target value. Thereafter, the control module 708, 902 multiplies the difference by the proportional gain coefficient value in the proportional gain parameter register 910, multiples the integral of the difference by the integration gain coefficient value in the integration gain parameter register 910, multiplies the derivative of the difference by the derivative gain coefficient value in the derivative gain parameter register 910, and sums the products to obtain a delivery command for operating the motor 710, 904. Thereafter, the delivery command is converted to one or more motor commands corresponding an amount of rotation of the rotor of the motor 710, 904 (e.g., a number of motor steps or the like) that displaces the plunger of the reservoir 712 to deliver, to the body 704 of the user, an amount of fluid corresponding to the delivery command. In this manner, the closed-loop PID control regulates the condition of the user to the target value maintained in the target parameter register 910 in accordance with the control scheme or algorithm stored in memory 908. Accordingly, subsequently measured values for the condition of the user obtained by the sensing arrangement 706 are influenced by the delivery command determined by the control module 708, 902, which, in turn, is influenced by the control information received from the monitoring device 804.

Still referring to FIG. 11, the illustrated process 1100 continues by determining whether the infusion device should provide updated measurement data for the condition of the user to the monitoring device (task 1116). In exemplary embodiments, the infusion device 802, 900 implement a timer or another feature that supports autonomously uploading the measurement data on a periodic basis. In this regard, the infusion device 702, 802, 900 may buffer or otherwise store (e.g., in memory 908) the measurement data most recently received from the sensing arrangement 706 over a particular duration of time, and once that amount of time has elapsed, automatically initiate an upload of the measurement data to the monitoring device 804. For example, the infusion device 702, 802, 900 may store measurement data received from the sensing arrangement 706 over a preceding five minute interval and upload the stored measurement data to the monitoring device 804 every five minutes. Additionally, as described above, in some embodiments, the infusion device 702, 802, 900 may also buffer or otherwise store delivery data for the same duration of time that corresponds to the measurement data and upload the delivery data to the monitoring device 804 along with the measurement data.

In response to determining that updated measurement data should be uploaded, the update process 1100 continues by establishing a peer-to-peer communication session with the client device, transmitting or otherwise providing the measurement data to the client device via the peer-to-peer communication session, and then terminating the peer-to-peer communication session (tasks 1118, 1120, 1122). The infusion device 802, 900 autonomously initiates the peer-to-peer communication session 814 by transitioning the transceiver module of the communications interface 906 from a low power mode to an active mode and transmitting or otherwise providing an indication of a desire to establish the peer-to-peer communication session 814 (e.g., a connection request) to the client device 806 via the first network 810. In response, the client device 806 and/or update module 807 initiates or otherwise establishes the peer-to-peer communication session 816 with the monitoring device 804 before providing a response to the infusion device 802, 900 that establishes the peer-to-peer communication session 814. In response to the peer-to-peer communication sessions 814, 816 being established, the infusion device 802, 900 automatically transmits the measurement data and delivery data to the client device 806 via the peer-to-peer communication session 814, and the client device 806 and/or update module 807 automatically retransmits, streams, or otherwise forwards the measurement data and delivery data received via the peer-to-peer communication session 814 to the monitoring device 804 via the peer-to-peer communication session 816 over the second network 812. In this manner, the infusion device 802, 900 autonomously pushes or otherwise uploads measurement data and delivery data to the monitoring device 804 via the client device 806.

In exemplary embodiments, after transmitting the measurement data, the infusion device 802, 900 transmits or otherwise provides a termination request to the client device 806 to terminate the peer-to-peer communication session 814 and delete or otherwise remove any measurement data from the client device 806. After transmitting all of the measurement data and receiving the termination request, the client device 806 transmits a confirmation to the infusion device 802, 900 indicating that the measurement data has been deleted from the client device 806 and that the peer-to-peer communication session 814 will be terminated, and terminates the peer-to-peer communication session 816 in response to termination of the peer-to-peer communication session 814. In response to the confirmation, the control module 902 may automatically transition the transceiver module of the communications interface 906 from the active mode to a low power mode thereby terminating the peer-to-peer communication session 814.

In exemplary embodiments, the update process 1100 continues operating the infusion device in accordance with the stored control information and periodically uploading measurement data to the monitoring device (e.g., tasks 1114, 1116, 1118, 1120, 1122) until receiving an indication of an update to the control information (e.g., task 1104). In this regard, recent (or new) measurement data that is influenced by the control information currently stored and/or implemented by the infusion device 802, 900 is periodically provided to the monitoring device 804, which, in turn, analyzes that recently obtained measurement data for that user in conjunction with historical measurement data and/or delivery data for that user stored in the database 808 to determine whether any control information should be adjusted. When the monitoring device 804 determines the control information for that user should be adjusted, the monitoring device 804 indicates or otherwise notifies the client device 806 and/or update module 807 to establish the peer-to-peer communication session 814. Thereafter, the update process 1100 repeats the steps of downloading the updated control information to the infusion device and updating the control information implemented by the infusion device as described above (e.g., tasks 1106, 1108, 1110, 1112). In this manner, the control information maintained by the infusion device may be dynamically updated in a user-specific (or patient-specific) manner based on that user's recent and historical measurement and delivery data to better accommodate lifestyle changes by the user and/or changes in the user's needs.

Figure 12:
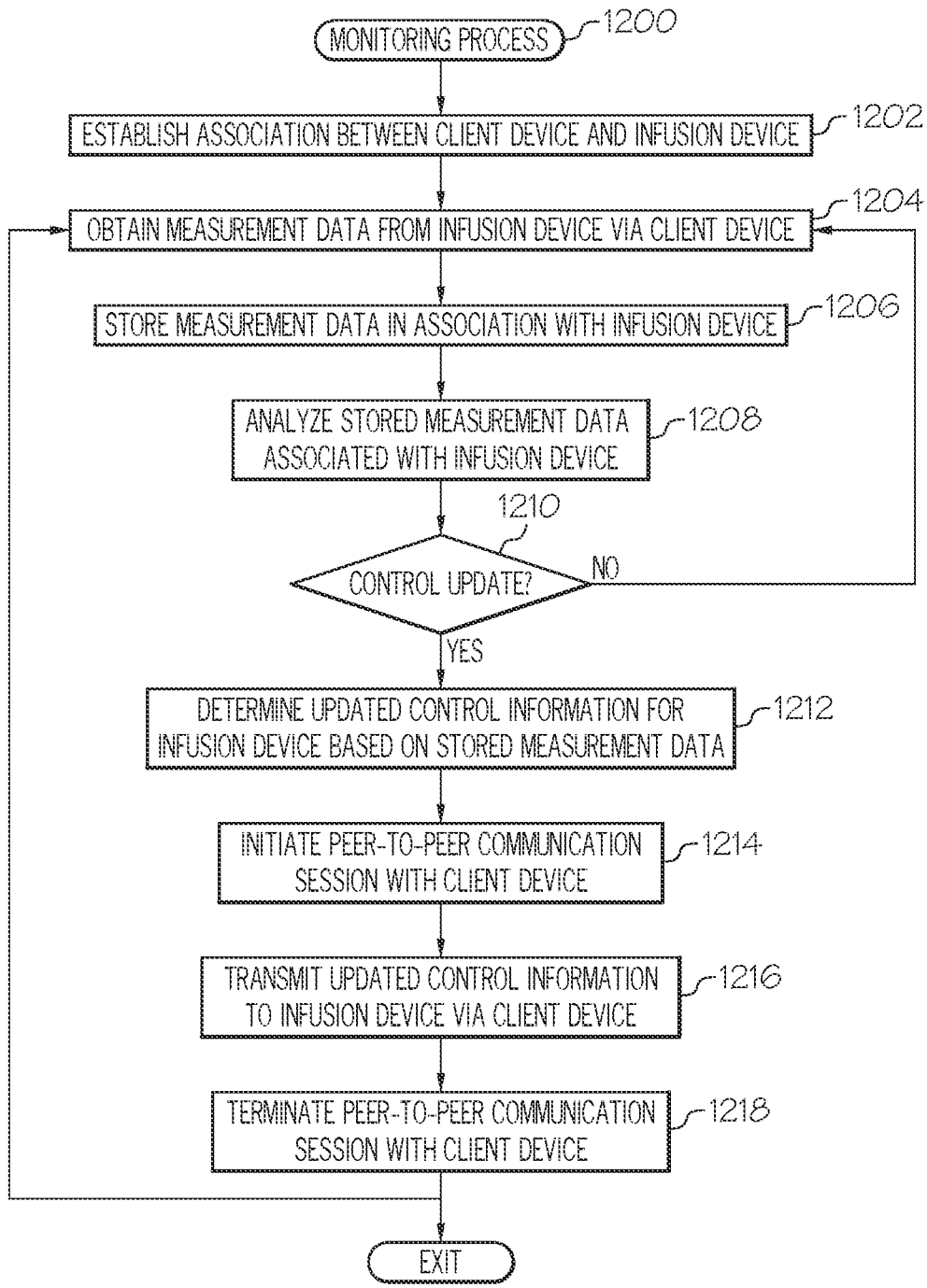
FIG. 12 is a flow diagram of an exemplary monitoring process suitable for use with the infusion system of FIG. 8 in conjunction with the update process of FIG. 11 to dynamically adjust the closed-loop control system using measurement data for the user in accordance with one or more exemplary embodiments.

FIG. 12 depicts an exemplary monitoring process 1200 suitable for implementation by a monitoring device in an infusion system to dynamically update the control scheme being implemented by a fluid infusion device based at least in part on measurement data associated with the user of that fluid infusion device. The various tasks performed in connection with the monitoring process 1200 may be performed by hardware, firmware, software, or any combination thereof. For illustrative purposes, the following description refers to elements mentioned above in connection with FIGS. 1-10. In practice, portions of the monitoring process 1200 may be performed by different elements of the infusion system 800; however, in exemplary embodiments described herein, the monitoring device 804 performs the monitoring process 1200. The monitoring process 1200 may include any number of additional or alternative tasks, the tasks need not be performed in the illustrated order and/or the tasks may be performed concurrently, and/or the monitoring process 1200 may be incorporated into a more comprehensive procedure or process having additional functionality not described in detail herein. Moreover, one or more of the tasks shown and described in the context of FIG. 12 could be omitted from a practical embodiment of the monitoring process 1200 as long as the intended overall functionality remains intact.

The illustrated process 1200 begins by establishing an association between a client device and a fluid infusion device and/or user (task 1202). As described above, in response to pairing the client device 806 with the infusion device 802, the client device 806 and/or update module 807 automatically communicates with the monitoring device 804 to identify its associated infusion device 802 and/or user. In response, the monitoring device 804 establishes or otherwise maintains an association between the client device 806, the infusion device 802, and/or the user wearing the infusion device 802 using the information received from the client device 806. For example, the client device 806 may establish a peer-to-peer communication session 816 with the monitoring device 804 over the second network 812 and provide the monitoring device 804 with the unique identifier(s) associated with the infusion device 802, 900 and/or the user wearing the infusion device 802, 900 along with identification information for the client device 806 on the second network 812. The network identification information for the client device 806 may include an address of the client device 806 on the second network 812, a unique identifier associated with the transceiver module or another hardware component of the client device 806 used to access the second network 812, a unique identifier associated with the client device 806 on the second network 812 (e.g., a mobile phone number, an international mobile station equipment identity number, or the like), and/or other information that may be utilized to uniquely identify and/or authenticate the client device 806 on the second network 812. The monitoring device 804 stores the network identification information for the client device 806 in the database 808 in association with the unique identifier(s) associated with the infusion device 802 and/or the user wearing the infusion device 802, thereby establishing and maintaining an association between the client device 806 and its associated infusion device 802 and/or user.

In the illustrated embodiment, the monitoring process 1200 continues by receiving or otherwise obtaining measurement data from the infusion device via its associated client device and storing or otherwise maintaining the measurement data in association with the infusion device (tasks 1204, 1206). For example, as described above, the infusion device 802 may periodically initiate the peer-to-peer communication session 814 with the client device 806 over network 810 to periodically upload measurement data and/or delivery data to the monitoring device 804. In response to the request for the peer-to-peer communication session 814 from the infusion device 802, the client device 806 and/or update module 807 automatically initiates the peer-to-peer communication session 816 with the monitoring device 804, for example, by transmitting a request for the peer-to-peer communication session 816 over the second network 812. The monitoring device 804 transmits or otherwise provides a response or acknowledgement of the request that establishes the peer-to-peer communication session 816 with the client device 806, which, in turn establishes the peer-to-peer communication session 814 with the infusion device 802.

Thereafter, the measurement data and/or delivery data is uploaded to the monitoring device 804 by the client device 806 automatically retransmitting measurement data and/or delivery data received from the infusion device 802 via the peer-to-peer communication session 814 to the monitoring device 804 via the peer-to-peer communication session 816 on the second network 812. The monitoring device 804 uses the stored identification information for the client device 806 on the second network 812 to identify the received measurement data and/or delivery data as being from the client device 806 associated with the infusion device 802 (e.g., by analyzing source information in a packet header), and thereby stores the received measurement data and/or delivery data in association with the infusion device 802, its associated user and/or the client device 806 using their respective stored identifiers. In exemplary embodiments, the client device 806 terminates the peer-to-peer communication session 816 after retransmitting the entirety of the measurement and delivery data received from the infusion device 802 to the monitoring device 804 and ensuring that the measurement and delivery data is deleted or otherwise removed from the client device 806.

In exemplary embodiments, the monitoring process 1200 continues by analyzing the recently received measurement data from an infusion device in conjunction with the previously stored measurement data from the infusion device to autonomously determine whether the control information for that infusion device should be updated, changed, or otherwise adjusted to better accommodate the needs of its associated user (tasks 1208, 1210). For example, depending on the embodiment, the monitoring device 804 may determine that the control information implemented by an infusion device 802 should be updated automatically when a particular duration of time has elapsed since the last time the control information was updated (e.g., for periodic updates), when an updated value for a control parameter deviates from the current value for that control parameter being implemented by the infusion device 802 by more than a threshold amount, or when a new control algorithm is available for being implemented by the infusion device 802 (e.g., a new release of control application code and/or an update to the existing application code). In this regard, for each particular infusion device 802 in the infusion system 800, the monitoring device 804 may store or otherwise maintain (e.g., in database 808) versioning information for the control application code being implemented by that infusion device 802 along with the values for control parameters that are currently being utilized by that infusion device 802 (e.g., the current gain coefficients and/or target value).

When the monitoring process 1200 determines that the control information for an infusion device should be updated, adjusted or otherwise modified, the monitoring process 1200 determines updated control information for the infusion device based on the stored measurement data and/or delivery data for its associated user (task 1212). For example, using the recently received measurement data and/or delivery data for the user along with the previously stored measurement data and/or delivery data for the user, the monitoring device 804 may calculate or otherwise determine updated PID gain coefficients, updated target values, and/or updated values for one or more other patient-specific control parameters as described above. In this regard, by utilizing relatively greater amounts of measurement data and/or delivery data that may be stored by the database 808 to determine the updated control information, the updated control information determined by the monitoring device 804 is likely to more accurately and/or reliably reflect the user's insulin response and/or requirements.

Once the updated control information is determined, the monitoring process 1200 continues by initiating establishment of peer-to-peer communication sessions with the client device and transmitting the updated control information to the infusion device via the peer-to-peer communication sessions with the client device (tasks 1214, 1216, 1218). In this regard, the monitoring device 804 initiates the peer-to-peer communication session 816 by transmitting or otherwise providing a request to the client device 806 and/or update module 807 via the second network 812, wherein in response, the client device 806 and/or update module 807 automatically attempts to initiate the peer-to-peer communication session 814 over the first network 810. In response to the peer-to-peer communication session 814 being established, the client device 806 and/or update module 807 provides a response, acknowledgment, or some other indication to the monitoring device 804 that establishes the peer-to-peer communication session 816. Once the peer-to-peer communication sessions 814, 816 are established, the monitoring device 804 automatically transmits the updated control information to the client device 806 via the peer-to-peer communication session 816 over the second network 812, wherein the client device 806 automatically retransmits the updated control information to the infusion device 802 via the peer-to-peer communication session 814 over the first network 810. After the monitoring device 804 has transmitted the entirety of the control information to the client device 806, the monitoring device 804 terminates the peer-to-peer communication session 816, which, in turn, causes the client device 806 to terminate the peer-to-peer communication session 814 with the infusion device 802. In this manner, the monitoring device 804 autonomously pushes updated control information to the infusion device 802. The loop defined by tasks 1204, 1206, 1208, 1210, 1212, 1214, 1216, and 1218 may repeat indefinitely throughout operation of an infusion device to dynamically update or otherwise adjust the closed-loop control being implemented by the infusion device to better accommodate the changes to the needs of its associated user.

In one or more embodiments, after transmitting the updated control information, the monitoring device 804 transmits or otherwise provides a termination request to the client device 806 to terminate the peer-to-peer communication session 816 and delete or otherwise remove any control information from the client device 806. After transmitting all of the control information and receiving the termination request, the client device 806 transmits a confirmation to the monitoring device 804 indicating that the control information has been deleted from the client device 806 and that the peer-to-peer communication session 816 will be terminated, and terminates the peer-to-peer communication session 814 in response to termination of the peer-to-peer communication session 816. In response to the confirmation, the monitoring device 804 may automatically terminate the peer-to-peer communication session 816.

Figure 13:
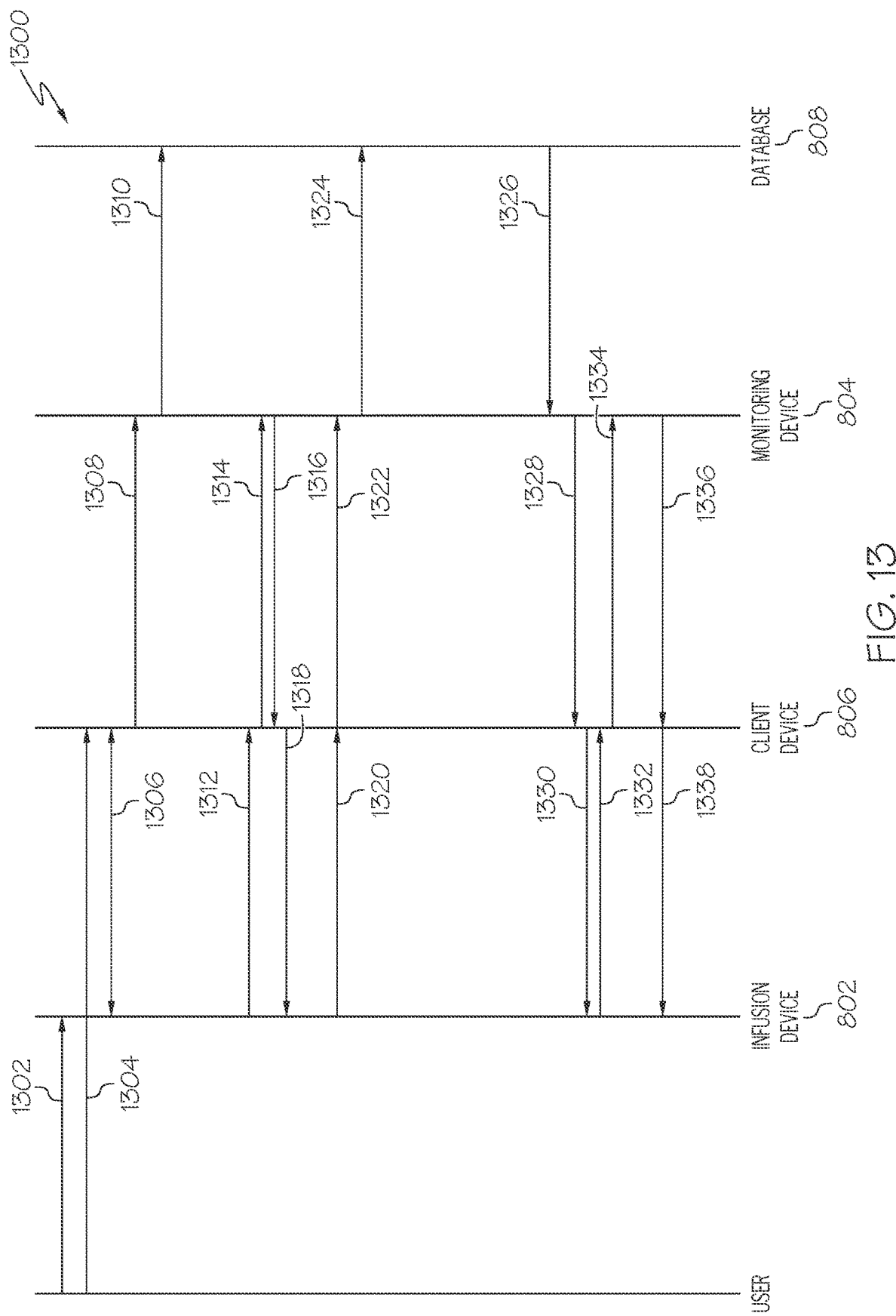
FIG. 13 depicts an exemplary sequence of communications within the infusion system of FIG. 8 in conjunction with the update process of FIG. 11 and the monitoring process of FIG. 12 and in accordance with one exemplary embodiment.

FIG. 13 depicts an exemplary sequence 1300 of communications within the infusion system 800 of FIG. 8 in connection with the update process 1100 of FIG. 11 and the monitoring process 1200 of FIG. 12. In exemplary embodiments, the user wearing the infusion device 802 manipulates 1302 the infusion device 802 to enable or otherwise activate its associated transceiver and manipulates 1304 the client device 806 enable or otherwise activate its associated transceiver so that the infusion device 802 and the client device 806 both communicate on the first network 810. For example, the user may manipulate the infusion device 802 to perform a discovery process on the first network 810 and manipulate the client device 806 so that it is discoverable on the first network 810, or vice versa. Thereafter, the infusion device 802 and the client device 806 communicate 1306 with one another on the first network 810 to establish an association with one another. In this regard, the infusion device 802 obtains and stores (e.g., in memory 908) identification information for the client device 806 on the first network 810, and the client device 806 obtains and stores identification information for the infusion device 802 on the first network 810 along with any unique identifiers associated with the infusion device 802 and/or its associated user. After establishing an association with the infusion device 802, the client device 806 establishes 1308 the peer-to-peer communication session 816 on the second network 812 and transmits or otherwise provides the unique identification information associated with the infusion device 802 to the monitoring device 804. For example, the update module 807 may use stored or preconfigured address information for the monitoring device 804 to establish the peer-to-peer communication session 816 on the second network 812. As described above, in addition to the unique identification information for the infusion device 802 provided by the client device 806, the monitoring device 804 also obtains identification information for the client device 806 on the second network 812. The monitoring device 804 maintains an association between the infusion device 802 and the client device 806 by storing 1310 the identification information for the client device 806 in association with the identification information for the infusion device 802 in the database 808.

To periodically upload new measurement data and/or delivery data to the monitoring device 804, the infusion device 802 utilizes the stored identification information for the client device 806 on the first network 810 to initiate the peer-to-peer communication session 814 by transmitting 1312 a connection request to the client device 806. In response, the client device 806 automatically transmits 1314 a connection request to the monitoring device 804. When the monitoring device 804 responds 1316 to establish the peer-to-peer communication session 816, the client device 806 automatically responds 1318 to the infusion device 802 to establish the peer-to-peer communication session 814. In response to establishing the peer-to-peer communication session 814, the infusion device 802 automatically transmits 1320 the measurement data and/or delivery data to the client device 806 via the peer-to-peer communication session 814, and the client device 806 automatically retransmits 1322 the measurement data to the monitoring device 804 via the peer-to-peer communication session 816. Using the association between the client device 806 and the infusion device 802, the monitoring device 804 stores 1324 the received measurement data and/or delivery data in association with the infusion device 802 and/or its associated user. It should be noted that, in exemplary embodiments, the new measurement data and/or delivery data is uploaded from the infusion device 802 to the monitoring device 804 via the client device 806 in an automated manner without any interaction being required on behalf of the user wearing the infusion device 802 and/or using the client device 806. As described above, in some embodiments, after transmitting the measurement data and/or delivery data to the client device 806, the infusion device 802 and the client device 806 may perform a termination procedure that requires the client device 806 to provide an acknowledgment or confirmation to the infusion device 802 that the measurement data and/or delivery data has been deleted or otherwise removed from the client device 806 before terminating the peer-to-peer communication sessions 814, 816.

To periodically update the control information implemented by the infusion device 802, the monitoring device 804 may periodically access or otherwise obtain 1326 the stored measurement data and/or delivery data associated with the infusion device 802 in the database 808 and analyze the measurement data and/or delivery data to determine updated control parameters for the infusion device 802. Thereafter, the monitoring device 804 utilizes the stored identification information for the client device 806 on the second network 812 to initiate the peer-to-peer communication session 816 by transmitting 1328 a connection request to the client device 806. In response, the client device 806 automatically transmits 1330 a connection request to the infusion device 802. When the infusion device 802 responds 1332 to establish the peer-to-peer communication session 814, the client device 806 automatically responds 1334 to the monitoring device 804 to establish the peer-to-peer communication session 816. In response to establishing the peer-to-peer communication session 816, the monitoring device 804 automatically transmits 1336 the updated control information to the client device 806 via the peer-to-peer communication session 816, and the client device 806 automatically retransmits 1338 the control information to the infusion device 802 via the peer-to-peer communication session 814. Thereafter, the infusion device 802 may update its stored control information, for example, by overwriting previous parameter values stored in the parameter registers 910 with updated parameter values. Again, it should be noted that the updated control information may be downloaded to the infusion device 802 from the monitoring device 804 via the client device 806 in an automated manner without any interaction being required on behalf of the user wearing the infusion device 802 and/or using the client device 806. Furthermore, in some embodiments, after transmitting the updated control information to the client device 806, the monitoring device 804 and the client device 806 may perform a termination procedure that requires the client device 806 provide an acknowledgment or confirmation to the monitoring device 804 that the control information has been deleted or otherwise removed from the client device 806 before terminating the peer-to-peer communication sessions 814, 816.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A system comprising:
one or more processors; and
one or more processor-readable storage media storing instructions which, when executed by the one or more processors, cause performance of:
associating a medical device with an intermediate device configured for automatic retransmission of data to the medical device;
obtaining, from the medical device via the intermediate device, measurement data correlative to a condition of a user;
determining updated control information for the medical device based at least in part on the measurement data;
receiving an acknowledgement from the intermediate device that a communication session has been established between the intermediate device and a monitoring device, wherein the intermediate device automatically provides the acknowledgement responsive to a second communication session being established between the intermediate device and the medical device; and
in response to receiving the acknowledgement from the intermediate device, streaming the updated control information to the medical device based on communicating the updated control information to the intermediate device such that the updated control information is not maintained on the intermediate device, wherein the medical device and a monitoring device that determines the updated control information for the medical device communicate on different types of communication networks, and wherein the intermediate device is configured to serve as an interface between the medical device and the monitoring device communicating on the different types of communications networks.

2. The system of claim 1, wherein the intermediate device and the medical device communicate via a peer-to-peer communication session.

3. The system of claim 1, wherein streaming the updated control information to the medical device based on communicating the updated control information to the intermediate device comprises:
establishing a first communication session with the intermediate device;
transmitting, via the first communication session, the updated control information to the intermediate device for the automatic retransmission to the medical device; and
after transmitting the updated control information, terminating the first communication session with the intermediate device.

4. The system of claim 3, wherein establishing the first communication session comprises:

causing establishment of a second communication session between the intermediate device and the medical device based on transmitting a connection request to the intermediate device; and receiving, from the intermediate device, a response indicative of the establishment of the second communication session between the intermediate device and the medical device.

5. The system of claim 4, wherein terminating the first communication session causes termination of the second communication session.

6. The system of claim 3, wherein terminating the first communication session comprises:

transmitting, to the intermediate device, a request to terminate the first communication session and to delete any of the updated control information stored on the intermediate device; and receiving, from the intermediate device, a confirmation indicating that the first communication session will be terminated, the confirmation further indicative of deletion of the any of the updated control information stored on the intermediate device.

7. The system of claim 1, wherein associating the medical device with the intermediate device comprises:

receiving, from the intermediate device, identification information for the medical device and the intermediate device; and maintaining the identification information in a database.

8. The system of claim 7, wherein the identification information comprises network identification information for the intermediate device.

9. The system of claim 1, wherein obtaining the measurement data comprises:

establishing a first communication session with the intermediate device;

receiving, via the first communication session, the measurement data from the medical device via the intermediate device;

maintaining the measurement data in association with the medical device; and after receiving the measurement data, terminating the first communication session.

10. The system of claim 9, wherein establishing the first communication session comprises:

receiving a connection request from the intermediate device; and causing establishment of a second communication session between the intermediate device and the medical device based on transmitting a response that establishes the first communication session.

11. The system of claim 9, wherein determining the updated control information comprises analyzing the measurement data in conjunction with previously stored measurement data.

12. A processor-implemented method, the method comprising:

associating a medical device with an intermediate device configured for automatic retransmission of data to the medical device;

obtaining, from the medical device via the intermediate device, measurement data correlative to a condition of a user;

determining updated control information for the medical device based at least in part on the measurement data;

receiving an acknowledgement from the intermediate device that a communication session has been established between the intermediate device and a monitoring device, wherein the intermediate device automatically provides the acknowledgement responsive to a second communication session being established between the intermediate device and the medical device; and in response to receiving the acknowledgement from the intermediate device, streaming the updated control information to the medical device based on communicating the updated control information to the intermediate device such that the updated control information is not maintained on the intermediate device, wherein the medical device and a monitoring device that determines the updated control information for the medical device communicate on different types of communication networks, and wherein the intermediate device is configured to serve as an interface between the medical device and the monitoring device communicating on the different types of communications networks.

13. The method of claim 12, wherein the intermediate device and the medical device communicate via a peer-to-peer communication session.

14. The method of claim 12, wherein streaming the updated control information to the medical device based on communicating the updated control information to the intermediate device comprises:

establishing a first communication session with the intermediate device;

transmitting, via the first communication session, the updated control information to the intermediate device for the automatic retransmission to the medical device; and after transmitting the updated control information, terminating the first communication session with the intermediate device.

15. The method of claim 14, wherein establishing the first communication session comprises:

causing establishment of a second communication session between the intermediate device and the medical device based on transmitting a connection request to the intermediate device; and receiving, from the intermediate device, a response indicative of the establishment of the second communication session between the intermediate device and the medical device.

16. The method of claim 15, wherein terminating the first communication session causes termination of the second communication session.

17. The method of claim 14, wherein terminating the first communication session comprises:

transmitting, to the intermediate device, a request to terminate the first communication session and to delete any of the updated control information stored on the intermediate device; and receiving, from the intermediate device, a confirmation indicating that the first communication session will be terminated, the confirmation further indicative of deletion of the any of the updated control information stored on the intermediate device.

18. The method of claim 12, wherein associating the medical device with the intermediate device comprises:

receiving, from the intermediate device, identification information for the medical device and the intermediate device; and maintaining the identification information in a database.

19. The method of claim 18, wherein the identification information comprises network identification information for the intermediate device.

20. One or more non-transitory processor-readable storage media storing instructions which, when executed by one or more processors, cause performance of:

associating a medical device with an intermediate device configured for automatic retransmission of data to the medical device;

obtaining, from the medical device via the intermediate device, measurement data correlative to a condition of a user;

determining updated control information for the medical device based at least in part on the measurement data;

receiving an acknowledgement from the intermediate device that a communication session has been established between the intermediate device and a monitoring device, wherein the intermediate device automatically provides the acknowledgement responsive to a second communication session being established between the intermediate device and the medical device; and in response to receiving the acknowledgement from the intermediate device, streaming the updated control information to the medical device based on communicating the updated control information to via the intermediate device such that the updated control information is not maintained on the intermediate device, wherein the medical device and a monitoring device that determines the updated control information for the medical device communicate on different types of communication networks, and wherein the intermediate device is configured to serve as an interface between the medical device and the monitoring device communicating on the different types of communications networks.

* * * * *